United States Patent [19]

Diack et al.

Best Available Copy

[11] E Re. 30,750

[45] Reissued Sep. 29, 1981

[54] CARDIAC RESUSCITATOR AND MONITORING APPARATUS

[75] Inventors: Archibald W. Diack; Warren S. Welborn, both of Portland; Robert G. Rullman, Beaverton, all of Oreg.

[73] Assignee: Cardiac Resuscitator Corporation, Lake Oswego, Oreg.

[21] Appl. No.: 148,159

[22] Filed: May 7, 1980

Related U.S. Patent Documents

Reissue of:

[64] Patent No.: 4,088,138
Issued: May 9, 1978
Appl. No.: 645,074
Filed: Dec. 29, 1975

U.S. Applications:

[63] Continuation of Ser. No. 429,745, Jan. 2, 1974, abandoned, which is a continuation-in-part of Ser. No. 253,507, May 15, 1972, abandoned.

[51] Int. Cl.[3] ..... A61N 1/36

[52] U.S. Cl. ..... 128/419 D; 128/419 PG; 128/639; 128/671; 128/784

[58] Field of Search ..... 128/419 D, 419 PG, 423, 128/671, 691, 639, 641, 642, 644, 650, 689, 693, 696, 702, 705, 706, 710, 711, 712, 715, 716, 721, 724, 784, 786, 787, 789, 791, 798

[56] References Cited

U.S. PATENT DOCUMENTS

| | | | |
|---|---|---|---|
| 569,380 | 10/1896 | Hollingsworth | 128/787 |
| 1,684,859 | 9/1928 | Catlin | 128/789 |
| 2,426,958 | 9/1947 | Ulsti, Jr. et al. | 128/644 |
| 2,949,910 | 8/1960 | Brown et al. | 128/715 |
| 3,030,946 | 4/1962 | Richards | 128/715 |
| 3,085,577 | 4/1963 | Berman et al. | 128/641 |
| 3,135,264 | 6/1964 | Tischler et al. | 128/423 |
| 3,144,018 | 8/1964 | Head | 128/642 |
| 3,144,019 | 8/1964 | Haber | 128/705 |
| 3,149,627 | 9/1964 | Bagno | 128/693 |
| 3,156,235 | 11/1964 | Jagger | 128/689 |
| 3,174,478 | 3/1965 | Kahn | 128/706 |
| 3,236,239 | 2/1966 | Berkovits | 128/419 D |
| 3,268,845 | 8/1966 | Whitmore | 128/721 |
| 3,306,298 | 2/1967 | Raimo | 128/351 |
| 3,316,902 | 5/1967 | Winchel et al. | 128/724 |
| 3,384,075 | 5/1968 | Mitchell | 128/706 |
| 3,442,269 | 5/1969 | Druz | 128/419 D |
| 3,460,542 | 8/1969 | Gemmer | 128/419 P |
| 3,499,435 | 3/1970 | Rockwell et al. | 128/671 |
| 3,547,108 | 12/1970 | Seiffert | 128/419 D |
| 3,572,317 | 3/1971 | Wade | 128/671 |
| 3,593,718 | 7/1971 | Krasner et al. | 128/419 PG |
| 3,611,801 | 10/1971 | Paine | 128/716 |
| 3,641,994 | 2/1971 | Gosling et al. | 128/691 |
| 3,703,900 | 11/1972 | Holzwagel | 128/419 PG |
| 3,716,059 | 2/1973 | Welborn et al. | 128/419 D |
| 3,734,094 | 5/1973 | Calinog | 128/642 |
| 3,746,004 | 7/1973 | Jankelson | 128/791 |
| 3,750,650 | 8/1973 | Ruttgers | 128/650 |
| 3,805,795 | 4/1974 | Denniston et al. | 128/419 D |
| 3,812,861 | 5/1974 | Peters | 128/798 |
| 3,857,398 | 12/1974 | Rubin | 128/419 D |
| 3,862,636 | 1/1975 | Bell et al. | 128/419 D |
| 3,866,615 | 2/1975 | Hewson | 128/419 D |
| 3,866,950 | 6/1975 | Ukkestad et al. | 128/419 D |
| 3,913,588 | 10/1975 | Klomp | 128/419 D |

FOREIGN PATENT DOCUMENTS

| | | |
|---|---|---|
| 285036 | 10/1970 | Austria . |
| 840567 | 4/1970 | Canada . |
| 869120 | 4/1971 | Canada . |
| 121090 | 9/1971 | Denmark . |
| 1067538 | 10/1959 | Fed. Rep. of Germany . |
| 6752096 | 3/1969 | Fed. Rep. of Germany . |
| 2118719 | 11/1972 | Fed. Rep. of Germany . |
| 2020437 | 7/1970 | France . |
| 2076891 | 9/1971 | France . |
| 2166812 | 7/1973 | France . |
| 7100758 | 6/1975 | Sweden . |
| 826766 | 1/1960 | United Kingdom . |
| 1224904 | 3/1971 | United Kingdom . |
| 1257114 | 12/1971 | United Kingdom . |
| 1261446 | 1/1972 | United Kingdom . |
| 1290537 | 9/1972 | United Kingdom . |
| 1313486 | 4/1973 | United Kingdom . |
| 1346495 | 2/1974 | United Kingdom . |

OTHER PUBLICATIONS

Sternlieb et al., "U.S. Armed Forces Medical Journal", vol. 11, No. 6, Jun. 1960, pp. 712–713.

Copland et al., "The Lancet", vol. 1, No. 7330, Feb. 22, 1964, p. 614.

Zoll et al., "Circulation", vol. 14, Nov. 1956, pp. 745-756.
Zoll et al., "Circulation", vol. 25, Apr. 1962, pp. 596-603.
Kouwenhoven et al., "American Journal of Physiology", vol. 100, 1932, pp. 344-350.
Stratbucker et al., "Rocky Mountain Engineering Society", 1965, pp. 57-61.
Stephenson, Jr., CV Mosby Co., 1974 pp. 374-377 & 336-337.
Stephenson, Jr., CV Mosby Co., 1971 pp. 336-337.
Lown et al., "Circulation", vol. 44, Oct. 1972, pp. 637-639.
Mirowski et al., "Archives of Internal Medicine",vol. 126, Jul. 1970, pp. 158-161.
News Release "Army", Surgeon General's Offices Scientific Breakthrough in Heart Device".

*Primary Examiner*—Wiliam E. Kamm
*Attorney, Agent, or Firm*—Chernoff & Vilhauer

[57] ABSTRACT

The disclosed apparatus attaches to the patient for monitoring the patient's condition and administering the correct electrical stimulation to a suspected heart attack victim as soon as possible after the occurrence of the attack and in the absence of medical personnel. The apparatus preferably includes an oro-pharyngeal airway provided with electrodes for ascertaining electrical activity of the heart. A microphone attached to the airway, or a strain gauge applied elsewhere to the patient's body, detects bodily motion, for example respiration. If neither substantial electrical activity nor bodily motion is detected, the patient is considered to be in a cardiac arrest and a pacing impulse is applied to the patient via the aforementioned airway electrodes and/or other electrodes, while if electrical activity is ascertained in the absence of bodily motion, a defibrillating pulse is applied to the patient.

41 Claims, 31 Drawing Figures

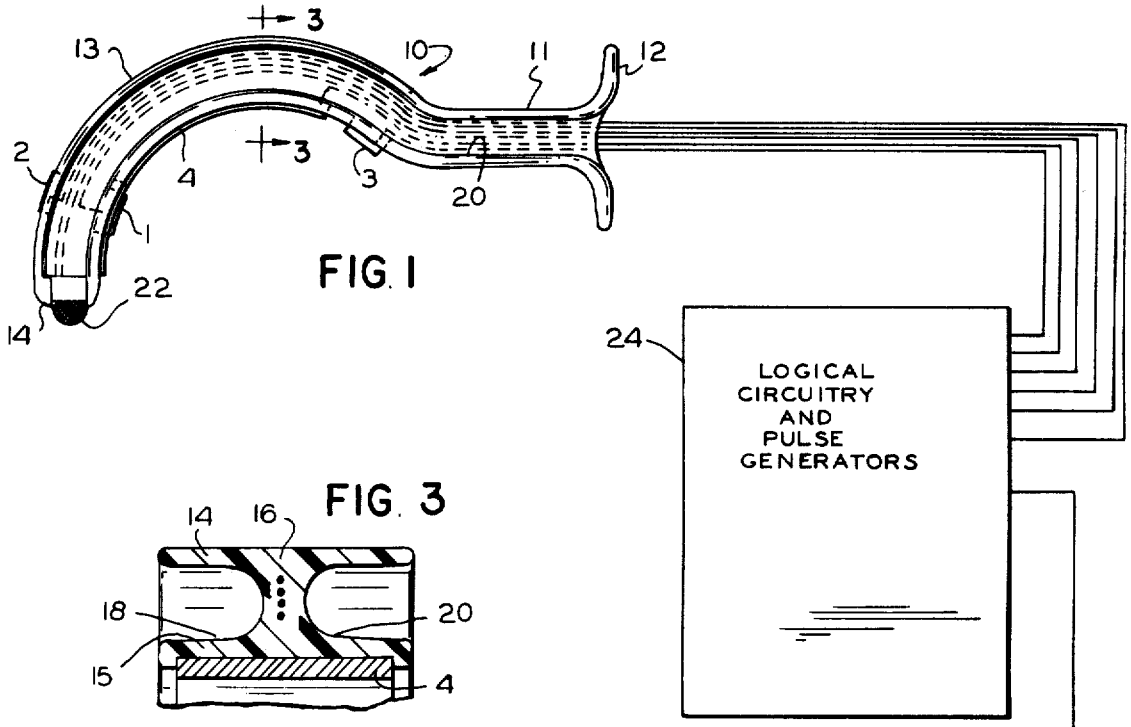
FIG. 1
FIG. 3
FIG. 2
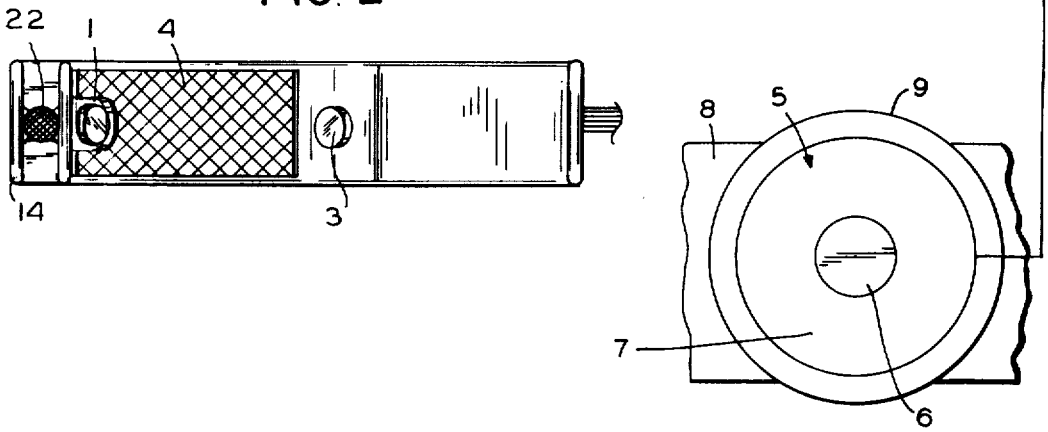

TABLE I

| EKG SENSOR | RESPIR. SENSOR | RESPONSE |
|---|---|---|
| + | + | NONE |
| + | 0 | DEFIB. |
| 0 | 0 | PACER |

FIG. 24
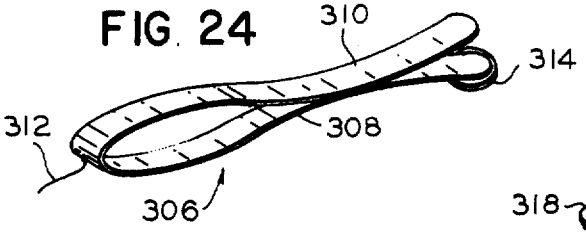
FIG. 25
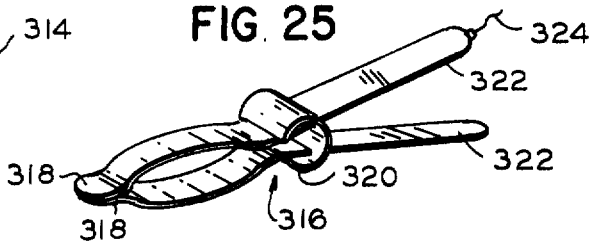
FIG. 26
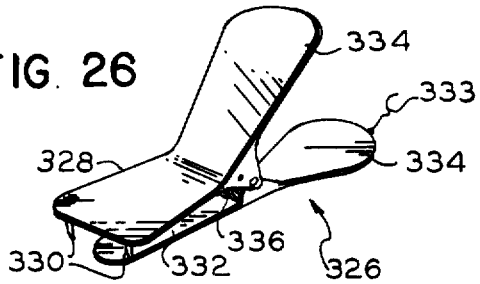
FIG. 27
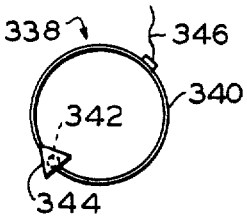
FIG. 28
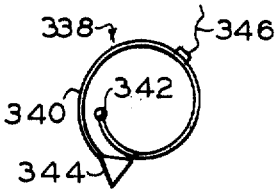
FIG. 30
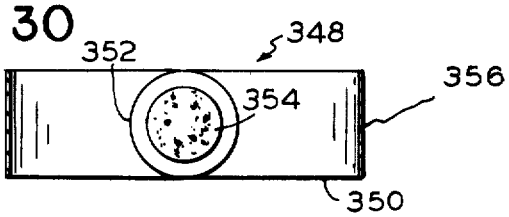
FIG. 29
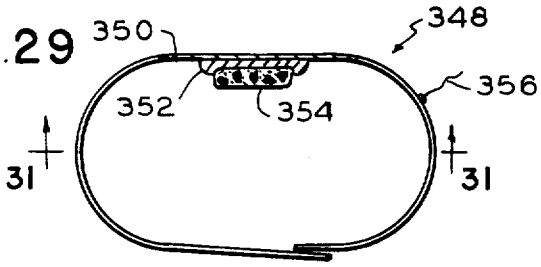
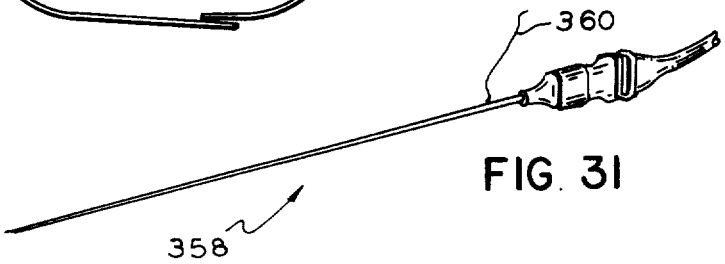
FIG. 31

CARDIAC RESUSCITATOR AND MONITORING APPARATUS

Matter enclosed in heavy brackets [ ] appears in the original patent but forms no part of this reissue specification; matter printed in italics indicates the additions made by reissue.

CROSS-REFERENCE TO RELATED APPLICATIONS

This [application is] *is an application for reissue of original patent No. 4,088,138, which, as an application, was* a continuation of copending U.S. Pat. application, Ser. No. 429,745, filed Jan. 2, 1974, by Archibald W. Diack, Warren S. Welborn and Robert G. Rullman, entitled "Cardiac Resuscitator and Monitoring Apparatus" and now abandoned, which was a continuation-in-part of copending U.S. Pat. application, Ser. No. 253,507, filed May 15, 1972, by Archibald W. Diack, Warren S. Welborn and Robert G. Rullman, entitled "Cardiac Resuscitator" and now abandoned.

BACKGROUND OF THE INVENTION

The present invention relates to cardiac resuscitator and monitoring apparatus and particularly to such apparatus which is securely attachable to a patient for rapidly ascertaining his cardiac condition for the purpose of bringing about corrective treatment.

An unusually large number of heart attack victims die each year as a result of delays in providing the intensive care required. A suspected heart attack victim must typically be hospitalized before receiving adequate medical attention. However, a great many patients suffering from coronary attack never reach the hospital. Cardiac arrests and arrythmias such as ventricular fibrillation frequently develop within a short time after the onset of the attack, e.g., within the first hour, with fatal results unless remedial steps are taken within minutes. Unless the normal rhythm can be restored to a heart in ventricular fibrillation within minutes, serious brain damage or death will result.

SUMMARY OF THE INVENTION

In accordance with the present invention, a cardiac resuscitator is provided which is compact enough for attachment to a suspected heart attack victim at nearly any location, and which may be operated by comparatively unskilled personnel. The resuscitator may be carried in an ambulance, for example, or may be conveniently stored in an industrial plant, office building, hotel, or the like, for immediate application to the suspected victim of a heart attack. In accordance with an embodiment of the present invention, a resuscitator includes first means for responding to electrical activity associated with the patient's heart, and second means for sensing bodily movement of the patient. Logical means respond to the first and second means for indicating the presence of electrical activity and whether bodily movement substantially accompanies such electrical activity. In the absence of either mechanical or electrical activity, a regular pacing impulse is applied to the patient. In the presence of detected electrical activity in the absence of bodily motion, a defibrillating pulse is applied. If both electrical activity and bodily motion are present, no corrective action is taken, although the equipment is suitably left attached to or near by the patient in case one of the aforementioned conditions develops before the patient is adequately hospitalized or under the care of adequately trained medical personnel.

In accordance with one embodiment of the present invention, a life sign monitoring system comprises an airway device adapted to be passed in or through the mouth and preferably into the pharynx of the patient, the airway having contact means mounted thereupon. In this case, first means connected to the contact means responds to electrical activity and second means senses bodily motion of the patient. Logical means responds to the indications for suitably supplying an output or for initiating appropriate operation of pacing or defibrillating means. Other external electrode means are suitably provided for attachment to the patient and cooperating to provide electrical input and output relative to the patient.

In the instance of a particular embodiment, the second means for sensing bodily movement advantageously comprises a sound detecting means or microphone mounted upon the aforementioned airway. Alternatively, the second means may comprise a sensor applied elsewhere to the body, and may comprise a strain gauge or the like applied to a belt or other appliance attached to the patient's chest. In either case, the mechanical motion output is indicative of a patient's respiration as a bodily motion life sign. Alternatively, bodily motion can be detected through detection of blood flow, phonocardiography, change in bodily impedance with a patient's pulse, or sensing temperature changes due to respiration.

When use of an airway is no longer possible, as when the patient becomes conscious, a mouth contacting clip or clamp is substituted therefor for monitoring purposes.

It is an object of the present invention to provide an improved cardiac resuscitator apparatus which may be applied to a suspected heart attack victim in nearly any location.

It is a further object of the present invention to provide an improved cardiac resuscitator apparatus which is securely attachable to a patient suffering from a suspected heart attack for the purpose of ascertaining electrical heart activity and bodily motion.

It is another object of the present invention to provide an improved life sign monitoring system applicable to a patient suffering from a suspected heart attack wherein required electrical connection to the patient can be rapidly and correctly initiated.

It is another object of the present invention to provide an improved life sign monitoring system for continued connection to a conscious patient.

It is a further object of the present invention to provide improved apparatus for ascertaining a plurality of life signs from a victim suffering a possible heart attack.

The subject matter which we regard as our invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

FIG. 1 is a view of a life sign monitoring and resuscitator system according to the present invention;

FIG. 2 is a bottom view of an oro-pharyngeal airway, 10, of FIG. 1;

FIG. 3 is a cross section of such airway taken at 3—3 in FIG. 1;

FIG. 24 is a perspective view of a clip device according to the present invention for insertion in the mouth of a patient in place of an airway;

FIG. 25 is a perspective view of a clamp device according to the present invention which may be attached either to the mouth of the patient, or elsewhere on the patient's body as an external electrode;

FIG. 26 is a perspective view of another clamping device according to the present invention for connection to the patient's body at an external location;

FIGS. 27 and 28 are top views of a ring device according to the present invention for connecting to a patient's extremity;

FIG. 29 is an end view of a ring or bracelet device according to the present invention also employed for connection to an extremity of a patient;

FIG. 30 is a cross sectional view taken at 30—30 in FIG. 29; and

FIG. 31 is a perspective view of an "IV" needle employed as an external electrode according to the present invention.

DETAILED DESCRIPTION

Figure 6:
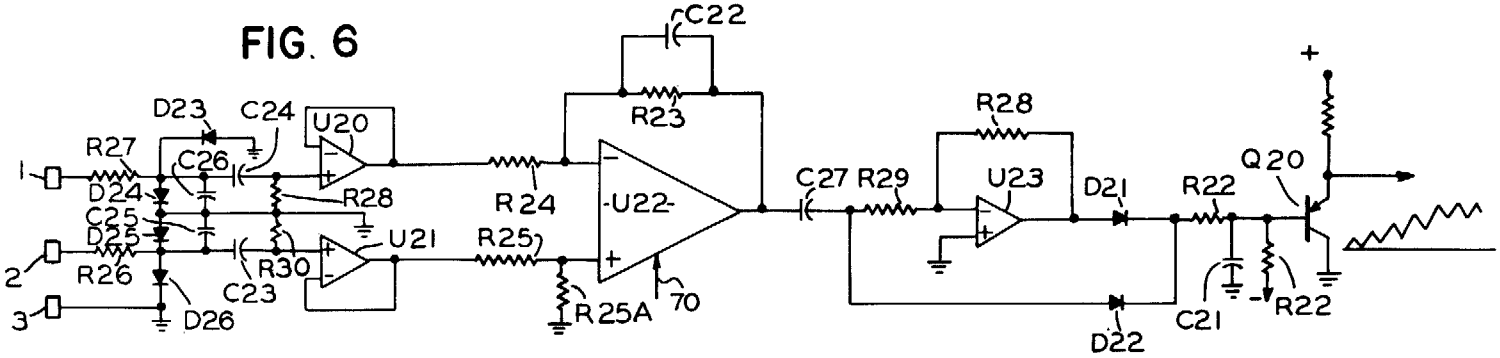
FIG. 6 is a schematic diagram of a circuit connectable to patient-contacting electrodes for providing output signals indicative of patient electrical heart activity, and including a Table I indicating corrective electrical stimulation applicable for different combinations of electrical activity and bodily motion conditions.

Referring to FIGS. 1 through 3, apparatus according to the present invention preferably includes an oropharyngeal airway 10 including a straight portion 11 and a curved, forward portion 13. The airway is formed of plastic and comprises a central, vertical web 16, extending substantially the full length of the airway, supporting an upper transverse flange 14 and the lower transverse flange 15 defining therebetween open-sided air passages 18 and 20 which are also open at the respective ends of the device to provide for communication of air from flanged end 12, exterior to the patient, to forward end 14. An airway as thus far described is frequently employed during administration of anesthesia and the like for maintaining a clear passageway into the patient's throat, the device being initially inserted through the patient's mouth and into the patient's pharynx. Such device is also frequently employed by a physician in providing mouth-to-mouth resuscitation.

In accordance with an embodiment of the present invention, the aforementioned airway 10 is further provided with first and second, or positive and negative, electrodes 1 and 2 positioned opposite one another on the outside flanges 15 and 14, respectively, near the forward end of the airway, and a neutral electrode 3 positioned on the curved part of flange 15 near straight portion 11 of the airway. These electrodes, formed of conductive material, are suitably round and partially embedded in the plastic from which the airway is made. An additional electrode plate 4 is disposed on the underside of the airway, i.e. on flange 15, substantially between the aforementioned electrodes 1 and 3. Electrode 4 is also formed of conductive material and is partially embedded in flange 15 while being completely insulated from the aforementioned electrodes 1 and 3. In one embodiment, the plate electrode 4 partially surrounds electrode 1 at the forward underside of the airway in spaced relation to electrode 1.

The airway is further supplied with a small microphone 22 mounted at the forward end 14 of the airway and secured upon the end of central web 16 in such a manner that the microphone does not block the passage of air on either side thereof. Substantially any type of small microphone may be employed which is substantially water-resistant, an encapsulated crystal microphone being suitable.

The various electrodes, as well as the microphone leads, are connected to logical circuitry and pulse generators 24 in a manner hereinafter more fully described. Also connected to the latter circuitry is additional or external electrode means 5 suitably comprising a relatively large circular electrode 7 mounted upon an insulating base 9 and further provided with a central, slightly raised electrode 6. The electrode means 5 is adapted for attachment to the patient elsewhere upon the patient's body, e.g. on the chest over the area of the heart or to an extremity. The electrode can be simply positioned or held against the patient, or may be attached to the patient by a belt 8 or other suitable clamping means. As will hereinafter be more fully described, electrode means 5 may be employed as an external input electrode for use in conjunction with input electrodes on the airway for ascertaining electrical activity of the heart, and may be employed in conjunction with electrode plate 4 for delivering a corrective stimulating pulse to the patient.

Briefly, an airway is inserted through the mouth of a patient who has undergone a suspected heart attack, and who is in an unconscious state. Electrode means 5 is positioned elsewhere on his body, preferably in the vicinity of the heart. The electrodes 1, 2 and 3 are adapted to provide, in conjunction with circuitry 24, an indication of electrical heart activity of the type suitable for providing an electrocardiogram. Circuitry 24 may, indeed, include conventional EKG equipment, but it is not always necessary, in accordance with the present invention, to develop the full EKG waveform of a patient's heart, but rather electrical activity alone can be detected by circuitry 24 and may be indicative of a normal heart waveform, or may be indicative of the erratic electrical heart output symptomatic of ventricular fibrillation. A second input is applied to circuitry 24 from microphone 22 and is indicative of sounds associated with bodily motion, i.e., sounds detected within the region of the patient's pharynx. In particular, the sound of any respiration or passage of air in the patient's throat will be detected by microphone 22. Secondarily, sounds associated with blood flow and/or the patient's heart beat or phonocardiogram can also be supplied by microphone 22. These sounds, indicative of bodily movement as a sign of life, are supplied to circuitry 24 in conjunction with the electrical signal hereinbefore mentioned, and the circuitry 24 is adapted to provide corrective electrical stimulation in accordance with the logical truth table, Table I in the drawings. If the electrical signal, indicated by the designation "EKG Sensor" in Table I, is present, and bodily motion according to the designation "Respiration Sensor" is also present, no corrective stimulating pulsation is delivered to the patient. If an electrical signal is present, and bodily motion is absent, a defibrillating pulsation may be delivered to the patient. However, if neither electrical nor bodily motion signal is present, cardiac arrest is indicated and a pacing pulse is delivered to the patient. The difference between a pacing pulse and a defibrillating pulse is well understood by those skilled in the art, a pacing pulse being adapted to restore heart action, e.g., in the case of a patient in the condition of cardiac arrest. A defibrillating pulse is adapted to inhibit erratic heart action in a patient wherein ventricular fibrillation is ascertained as evidenced by electrical output from the heart and no mechanical motion, e.g., respiration or pulse. The defibrillating pulse is normally at least an order of magnitude greater in current than the pacing pulse and is adapted temporarily to interrupt the functioning of the heart, after which a normal pulse frequently follows. Either the defibrillating or pacing pulse, as the case may be, is suitably applied between electrode plate 4, or one of the other electrodes on the airway 10, and electrode means 5 applied elsewhere to the patient's body.

Airway 10 is adapted to make relatively certain and immediate contact with the patient in respect to ascertaining an electrical signal as well as ascertaining an audible sound indicative of respiration or the like. It has been found that the EKG signal can be derived from electrodes mounted on an airway, and mounting the same in this location provides the advantage of rapid and certain electrical connection of these electrodes to the patient in an area where conduction is advantageously enhanced. Thus, the danger of failing to derive an electrical signal because of improper connection of electrodes to the patient is minimized.

According to one embodiment of the present invention, external electrode means 5, located elsewhere on the patient, is employed in combination with the airway electrodes for delivering the corrective electrical stimulation to the patient in response to the logical determination. The corrective pulsation is suitably applied across or between electrode means 5 and electrode plate 4. The utilization of the external electrode means 5 is adapted to supply corrective stimulation closer to the region of the patient's heart. Furthermore, although an oro-pharyngeal airway is illustrated and described, similar airway devices may be alternatively employed such as a nasal-pharyngeal airway or an intratracheal tube or devices coming under the general heading of catheters or catheter-like devices may be employed.

Figure 5:
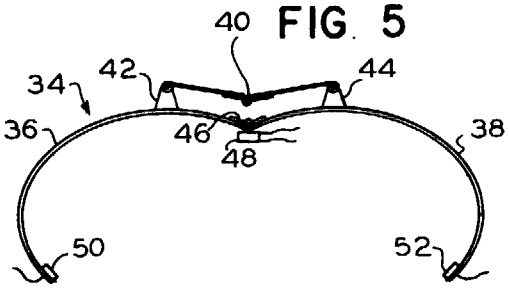
FIG. 5 is a side view of modified apparatus for ascertaining patient life signs and/or providing corrective electrical stimulation to the patient.
Figure 4:
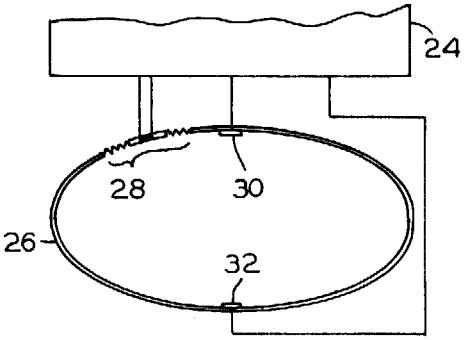
FIG. 4 is a side view of further apparatus for providing life sign monitoring signals and/or for applying corrective impulses to a patient.

Further means for ascertaining physical motion of the patient as a life sign are illustrated in FIGS. 4 and 5. In FIG. 4, a belt 26, which may be partially elastic in nature, is strapped to the patient's chest, such belt being provided with strain gauge means 28 for connecting the ends of the belt. The strain gauge means may be of any suitable type such as a variable resistance strain gauge or semiconductor strain gauge. The electrical terminals of such strain gauge are connected to circuitry 24 providing a substitute or additional indication of the patient's bodily motion. For example, with the belt 26 strapped to the patient's chest, the expansion and contraction associated with respiration will vary the resistance across the strain gauge means and supply an appropriate input to circuitry 24. In the event a belt 26 is utilized, EKG electrodes 30 and 32 are suitably also connected to circuitry 24 to provide a substitute or additional EKG electrical input to circuitry 24. Electrodes 30 and 32 can also be used as one or both of the electrodes for supplying stimulating pulses to the patient. For instance, electrode 30 suitably functions as electrode means 5. Sound sensing devices or microphones may be located at positions of electrodes 30 and 32 on the belt for providing a phonocardiogram input for ascertaining physical motion in a patient, i.e., the heart beat sound, and in the instance of a pair of microphone transducers, the blood flow can be ascertained indicative of patient movement by Doppler effect as understood by those skilled in the art.

A further apparatus advantageously employed for ascertaining bodily motion of the patient is illustrated in FIG. 5 at 34. This apparatus comprises a pair of flexible plastic tongs 36 and 38 formed in the arcuate manner as illustrated, and joined by means of hinge 46. Tongs 36 and 38 carry electrodes 50 and 52 at their remote ends, wherein these electrodes are suitably formed of a conducting sponge material. The tongs function in a spring-like manner for making firm contact with the patient, while a third electrode 48 supported from hinge 46 is adapted to rest upon the patient's chest. Electrodes 50 and 52 contact the lower right and left sides of the patient. Electrode 48 is also formed of a conductive sponge material of a known type wherein the resistance between the front and back face of the sponge is reduced as the same becomes compressed. In the present instance, sponge electrode 48 can function as a strain gauge the resistance of which changes with the patient's respiration. It is adapted to provide an input to circuitry 24 in the same manner as strain gauge 28 described in connection with FIG. 4.

Apparatus 34 is further supplied with brackets 42 and 44 attached to the back of tongs 36 and 38, respectively, wherein the remote ends of brackets 42 and 44 are pivotally connected to a hinge mechanism 40 adapted to lock and not rotate beyond the position shown. The hinge mechanism 40 thus functions as an over-center locking mechanism when the hinge mechanism 40 is depressed towards the patient's chest and into the position illustrated in FIG. 5. For removal of the apparatus from the patient, hinge mechanism 40 is upraised, for rotating brackets 42 and 44 toward one another, whereby tongs 36 and 38 are rotated away from the patient. As can be easily seen, initial attachment of this apparatus to the patient is accomplished by reversing the above procedure. Electrodes 50 and 52 can be used together or in combination with electrode 48 for making electrical contact with the patient and deriving the electrical EKG signal produced by the patient's heart. Furthermore, such electrodes can be employed for delivering the corrective heart stimulus to the patient, i.e., either a pacing or defibrillating pulse. Thus, the apparatus of FIG. 5 may be applied alone, or in conjunction with the airway apparatus illustrated in FIG. 1 for ascertaining electrical activity of a patient's heart as well as physical movement of the patient, and can then be employed either alone or in conjunction with the airway of FIG. 1 in applying corrective stimulating electrical impulses to the patient. The apparatus of FIG. 5 substantially substitutes for the FIG. 4 belt and electrode construction and has the advantage of not requiring the extension of a belt or the like completely around the patient. It is thus adapted for easier and quicker patient application.

FIG. 6 illustrates circuitry for ascertaining the electrical activity of a patient's heart and represents a portion of the circuitry to be found within the means indicated at 24 in FIG. 1. The input is thus provided at terminals 1, 2 and 3 which may correspond to similarly numbered electrodes 1, 2 and 3 mounted upon the airway 10 in FIG. 1 especially when an airway alone is used, although it is clear other electrode combinations placed elsewhere on the body as herein described may be employed. Terminal 3 in FIG. 6 represents a ground, neutral, or indifferent electrode and may be connected elsewhere on a patient's body such as to an extremity or may be coupled to electrode 3 in FIG. 1. Terminals 1 and 2, respectively, represent the positive and negative input electrodes. A differential circuit is herein described, although it is clear in certain instances that a single-ended circuit may be used.

Although the various electrode combinations may be employed for ascertaining the electrical activity of a patient's heart such as electrodes located solely upon the airway 10, it is preferred to employ an electrode or electrodes mounted on airway 10 in conjunction with the external electrode means such as illustrated at 5 positioned elsewhere on the body for example in the region of the chest, abdomen, or one of the extremities of the patient, such as a limb. Specifically, one of the input terminals, e.g. terminal 1, in FIG. 6 is suitably connected to one or more of the electrodes on airway 10 in FIG. 1, for example to electrodes 1 and 2, or 1, 2 and 3, while the input terminal designated by the numeral 2 in FIG. 6 is connected to the electrode means 5 and specifically to electrodes 6 and 7 thereof. The neutral or indifferent input terminal 3 in FIG. 6 may be connected to another point or extremity on the human body, or to a metal examining table or the like in the case where the patient resides on a metal support of this type. In the case of a "single ended" input, the neutral or indifferent terminal 3 in FIG. 6 is left unconnected, or the electrode means 5 is connected to terminal 3 in FIG. 6 rather than to terminal 2 in FIG. 6. In general, then, for the derivation of the strongest EKG signals, an airway is preferably employed in conjunction with an external electrode means such as illustrated at 5. Other external electrode means, for making a quick and easy connection to the patient for supplying requisite circuit continuity without delay are described in respect to the devices of FIGS. 25 through 31.

Terminal 1 is here coupled to a first input of a unity gain isolation amplifier U20 through the series combination of resistor R27 and capacitor C24. The junction between the resistor and capacitor is returned to ground via oppositely poled diodes D23 and D24 as well as capacitor C26, while the resistor R28 returns the positive or non-inverting input of amplifier U20 to ground. Resistor R27 and capacitor C26 form a low pass filter for filtering high frequency artifacts from the electrical input, and the combination of capacitor C24 and R28 provides sufficient differentiation to block low frequency level shifting disturbances from interfering with measurements. A similar combination of components function in substantially the identical manner in combination with unity gain isolation amplifier U21, wherein resistor R26 and capacitor C23 in series couple electrode 2 to the amplifier, with the center tap between those two components being returned to ground via diodes D25, D26, and capacitor C25. Diodes D23, D24, D25 and D26 protect the circuit from pacing and defibrillating pulses as may be applied to the patient via electrodes 1, 2 and 3 or other electrodes. A resistor R30 returns the noninverting input of amplifier U21 to ground.

The outputs of amplifiers U20 and U21 are coupled to inverting and noninverting inputs of differential amplifier U22 via resistors R24 and R25, the noninverting input being returned to ground by resistor R25A. Amplifier U22 also receives another input, 70, employed for clamping or disabling the amplifier as hereinafter mentioned. The feedback resistor R23 in shunt with capacitor C22 couples the output of amplifier U22 to the inverting input. Capacitor C22 is employed in removing residual high frequency components.

The output of amplifier U22 may be either a positive or negative-going pulse. Amplifier U23 and diode D21, coupled in cascade with the output of the amplifier, together with diode D22, form a push-pull, positive-going detector. The gain of amplifier U23 is arranged to be substantially unity, wherein resistor R29 connected in series with the inverting input of the amplifier, and resistor R28, in feedback relation to the amplifier, are of equal value.

A coupling capacitor C27 couples the output of amplifier U22 to the junction of resistor R29 and the anode of diode D22, wherein the cathode of diode D22 is connected in common with the cathode of diode D21, the latter having its anode driven from amplifier U23. The common outputs of diodes D21 and D22 are coupled to an integrating circuit comprising resistor R22 in series between the common diode-cathode connection and the ungrounded terminal of capacitor C21. A further resistor R22 returns the ungrounded capacitor terminal to a negative voltage. The integrating circuit provides further protection in the presence of high frequency artifacts and moreover requires several electrical input pulses from the input electrodes for providing an output of predetermined level at the emitter of output emitter-follower transistor Q20. Circuit time constants are adjusted such that a pulse rate of no less than approximately 20 to 30 per minute is required to achieve an output level sufficient to be acceptable in energizing the logic circuitry to which the emitter of transistor Q20 is connected. The emitter of transistor Q20 is connected to terminal 54 of the FIG. 7 logic circuit.

Figure 10:
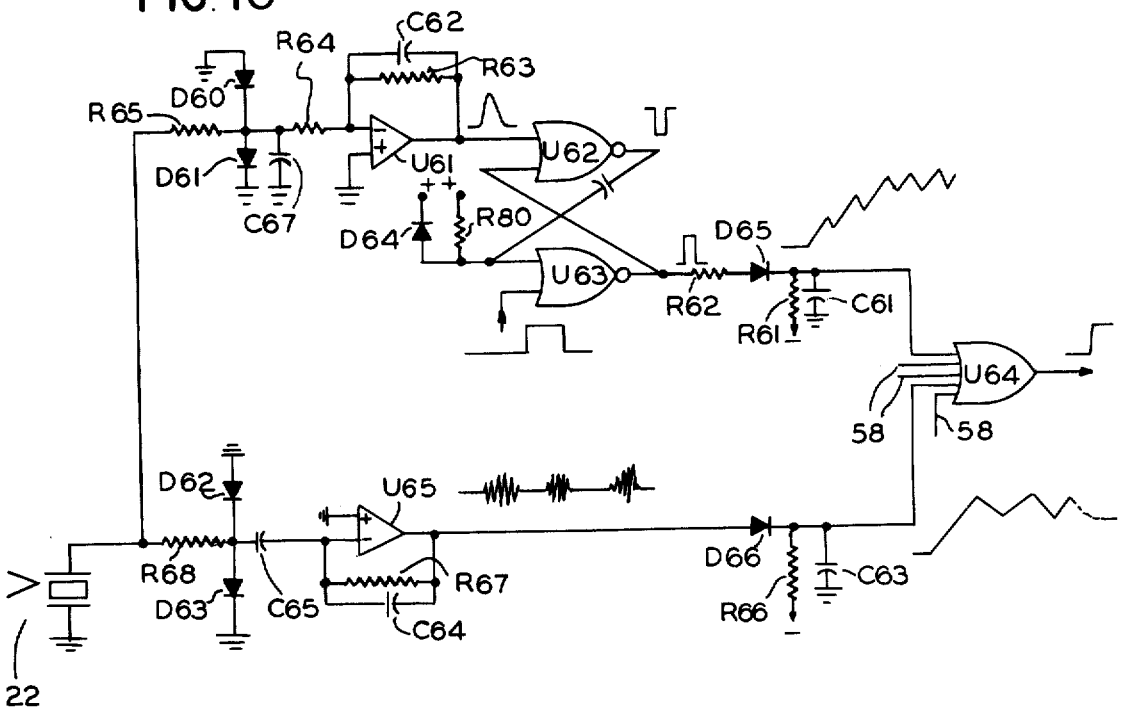
FIG. 10 is a schematic diagram illustrating circuitry responsive to bodily movement as indicated by respiration and/or pulse sounds.

Referring to FIG. 10, a first circuit is illustrated for ascertaining bodily movement or physical activity in a patient. In particular, the FIG. 10 circuit involves a microphone 22 which is responsive to breath sounds and pulse sounds in establishing the presence or absence of physical motion in the patient. As hereinafter mentioned, the microphone 22 is suitably attached at the forward end of airway 10 in FIG. 1. Microphone 22 is coupled to the inverting input of amplifier U65 via resistor R68 in series with capacitor C65, and the amplifier is shunted by the parallel combination of resistor R67 and capacitor C64. Diodes D62 and D63 are reversely poled, connecting the junction beween resistor R68 and capacitor C65 to ground for signals greater than diode drop. High frequency breath sounds are filtered and passed by a bandpass filter comprising the combination of resistor R67 and capacitor C65 as well as the combination of components R68 and C64. These sound packets, indicated by the waveform at the output of amplifier U65, are detected by diode D66 having its anode connected to the output of amplifier U65 and its cathode connected to the ungrounded terminal of capacitor C63. A resistor R66 further returns the junction of the diode and capacitor to a negative voltage. The combination of elements D66, R66 and C63 form an integrating circuit adapted to provide an output sufficient for operating or-gate U64 in the event of respiration packets or signals having greater than a designated repetition rate. The time constant of the circuit is such that the or-gate U64 will cease to be energized if 30 seconds pass without a respiration-indicating input being received at the microphone. The output of or-gate U64 is supplied to terminal 56 of the FIG. 7 logic circuit.

Although the lower part of the FIG. 10 circuit may be used alone, the same microphone may also be connected to detect bodily motion in the form of pulse or heart beat sounds. As indicated, microphone 22 can also be coupled via resistor R65 in series with resistor R64 to the inverting input of amplifier U61 shunted by means of resistor R63 in parallel with capacitor C62. Diodes D60 and D61 are oppositely poled and disposed between the junction of resistors R64 and R65 and ground, while a capacitor C67 is similarly disposed between the same junction and ground. The low frequency pulse sounds are passed by a filter comprising the resistors R64, R65 and capacitor C62. These pulse signals are amplified by amplifier U61 and are normalized with respect to width and amplitude by a flip-flop comprising nor-gates U62 and U63 cross-coupled in conventional feedback fashion to provide a one-shot multivibrator. The feedback input of nor-gate U63 is returned to a positive voltage by the parallel combination of clamping diode D64 and resistor R80, while the remaining input of U63 receives a gating input pulse as hereinafter described. A pulse sound input as derived from microphone 22 will cause a positive-going output of predetermined amplitude and duration at the output of nor-gate U63, assuming the lower or gating input of nor-gate U63 is not up. The positive-going output pulse is supplied via the series combination of resistor R62 and diode D65 to the ungrounded terminal of capacitor C61. A resistor R61 returns the junction of the diode and the capacitor to a negative voltage point. The circuit has a charge time constant that attenuates spurious artifact signals and also determines a minimum acceptable pulse rate, for example, a pulse rate of 20 to 30 per minute. A pulse rate as determined by this time constant circuit will then supply an energizing input to or-gate U64. It is noted that any input to or-gate U64 provides sufficient indication of bodily motion for the purpose of providing such indication to the logic circuit. Other inputs to or-gate U64 indicated at 58 may be derived from other circuitry, hereinafter described, which provides indication of bodily motion, and any of the inputs may be employed alone or in combination.

Figure 7:
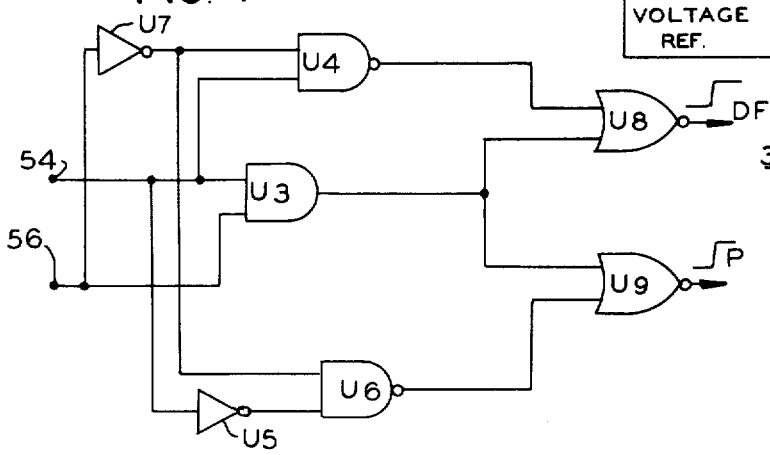
FIG. 7 is a logical diagram of circuitry according to the present invention for implementing the logical determination according to the Table I.

Considering now the logic circuit of FIG. 7, this circuit is designed to fulfill the logic requirements indicated in Table I. The input lead 54 is connected as an input to nand-gate U4 and to and-gate U3. Input lead 54 is also connected as an input to nand-gate U6 via inverter U5. Input 54 is indicative of electrical activity or EKG activity associated with the patient's heart. As hereinbefore indicated, a prescribed level of input on terminal 54 is necessary for operating any of the components to which terminal 54 is connected in FIG. 7.

Input lead 56 is connected as an input to and-gate U3, as well as an input to nand-gate U4 via inverter U7 and an input to nand-gate U6 via inverter U7. An input at 56 of predetermined level is indicative of a further life sign indication in the form of bodily movement sensed through sound detection of respiration, through phonocardiography, or through one of the other indications of bodily motion as hereinbefore and hereinafter described. It will be observed that if both an electrical activity indicating signal is present at terminal 54 and a bodily motion signal is present at terminal 56, a high output is supplied from the output terminal of nand-gate U4, a high output is provided at the output terminal of and-gate U3, and a high output is provided at the output terminal of nand-gate U6. Both nor-gates U8 and U9 are then supplied with inputs such that their outputs are low i.e., neither the positive level output "DF" or the positive output "P" will be present. Now if electrical activity is present, indicated by an input at terminal 54, and bodily movement is absent as indicated by an absence of an output at terminal 56, nand-gate U4 will be energized at both its terminals to provide a low output. Since only one input of and-gate U3 is energized, the output of U3 will be low. Consequently, the output of nor-gate U8 will be high providing a "DF" level indicative of a defibrillation condition or electrical activity in the absence of bodily motion. If, on the other hand, neither electrical activity nor bodily movement are present, the output of nand-gate U4 will be high and the output of and-gate U3 will be low. Since one high input is provided nor-gate U8, the output thereof will be low. However, since the inputs of nand-gate U6 are supplied via inverters U5 and U7 from terminals 54 and 56, both inputs of nand-gate U6 are up and consequently this output is low. Inasmuch as both the inputs of nor-gate U9 are low, the high level "P" output of U9 is present, indicating the desirability of providing a pacing pulse to the patient's heart since neither substantial electrical activity or bodily motion are present.

Figures 12, 13:
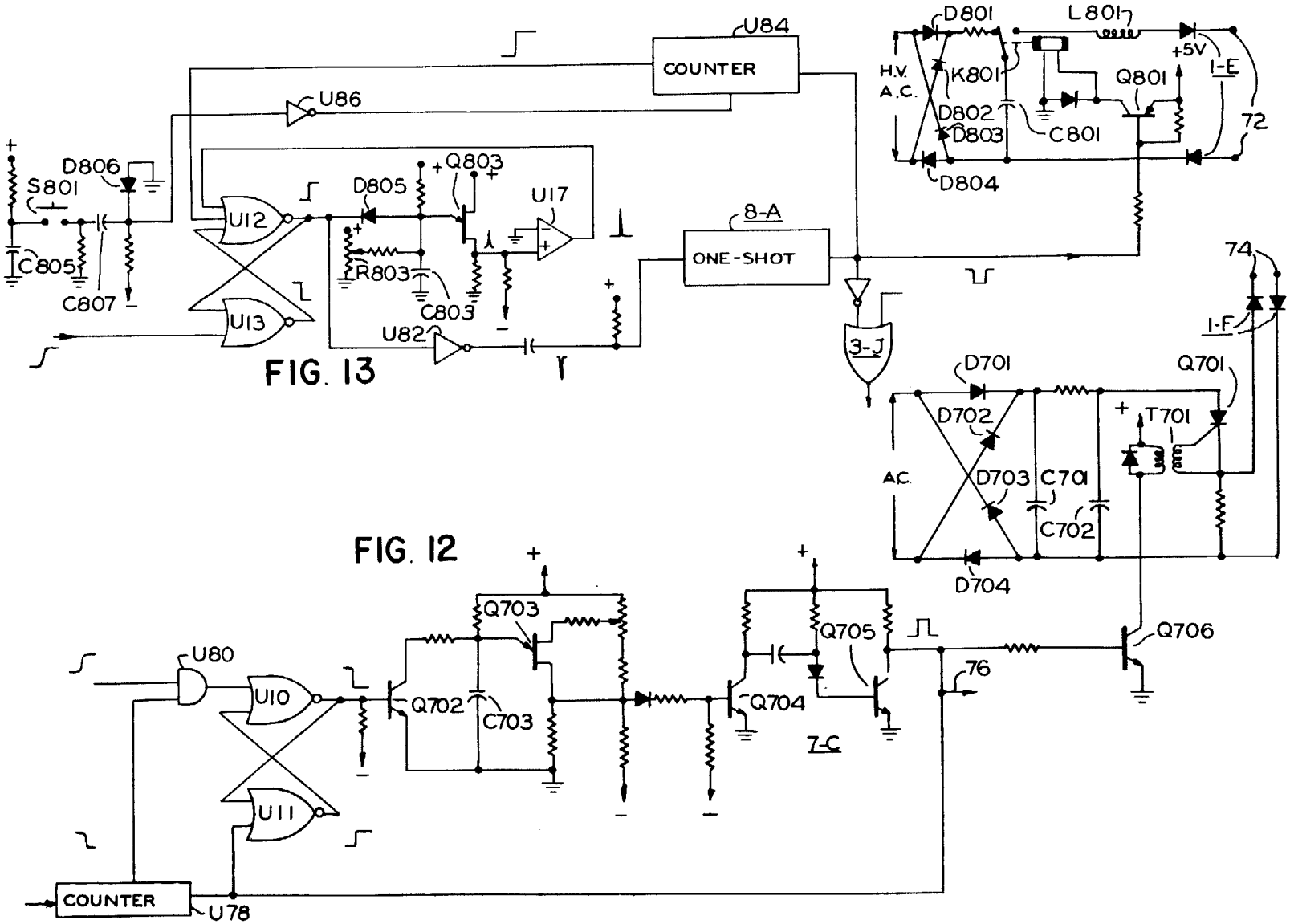
FIG. 12 is a schematic diagram of a circuit for generating pacing pulses for application to a patient.
FIG. 13 is a schematic diagram of a circuit for generating defibrillating pulses for application to a patient.

The circuitry for generating the pacing and defibrillating pulses for application to the patient in response to these logical outputs is illustrated in FIGS. 12 and 13, showing pacing and defibrillating circuitry respectively.

Referring first to FIG. 12, illustrating pacing circuitry, and-gate U80 receives an input at the input lead shown in full line from nor-gate U9 shown in FIG. 7. The remaining input to and-gate U80 is normally up and consequently the input signal level from gate U9 is applied as an input to nor-gate U10. Nor-gates U10 and U11 are cross-connected as a flip-flop, with the input from and-gate U80 causing the output of nor-gate U10 to go low and the output from nor-gate U11 to go high. When the output of nor-gate U10 goes low, capacitor C703, theretofore substantially shunted by transistor Q702, will start to charge toward a positive voltage. The pacer timer comprises a unijunction transistor Q703 having the capacitor C703 coupled between its emitter terminal and lower base. This circuit is a relaxation oscillator wherein the period thereof is suitably approximately 0.85 seconds. The unijunction transistor periodically discharges capacitor C703 to supply a pulse output at the lower base of the unijunction transistor. If the input at the base of transistor Q702 should later go high, transistor Q702 would be rendered conducting, and short capacitor C703 causing substantially immediate discharge thereof, and operation of the unijunction oscillator would be stopped. However, when the input of transistor Q702 goes low again, the oscillator will be restarted. The output of the timer is supplied to one-shot multivibrator 7-C, including transistors Q704 and Q705. The output at the collector of transistor Q705 is a series of positive pulses, each pulse suitably having a duration of about 100 milliseconds. This output may be connected as the right-hand input of or-gate 3-J in FIG. 13 via lead 76 for disabling or gating off certain circuitry when a pacing pulse is being generated.

The output of one-shot multivibrator 7-C is also applied as a resetting input to nor-gate U11 causing the output of nor-gate U11 to go low. If the input provided to gate U80 from the nor-gate U9 in FIG. 7 has gone low, the flip-flop comprising U10 and U11 will change states. This resetting option gives the circuitry the opportunity to completely reset and turn off should normal heart functioning or at least the absence of the need of a pacing pulse be detected by the presence of a normal beat between pacing pulsations. Should the input provided gate U80 from the FIG. 7 circuit still be up, the resetting option will have no effect. A counter U78 may be employed for counting the outputs of multivibrator 7-C and for locking out the circuit by providing a step-wave negative-going lower input to and-gate U80 after a predetermined large number of pacing pulses. The counter U78 may be reset manually as hereinafter more fully described or automatically from the output of gate U3 in FIG. 7 when normal heart activity is restored.

The output of the one-shot multivibrator 7-C is further applied via transistor Q706 as the input of pulse transformer T701, the secondary of which is coupled to provide the input of thyristor Q701. AC voltage from a power supply is normally applied across a bridge circuit comprising diodes D701, D702, D703 and D704 connected in DC charging relationship to capacitors C701 and C702, with thyristor Q701 being interposed between the positive end of capacitor C702 and connections 74 coupled for applying the impulse output to the patient. Thus, when transistor Q706 turns on, current flow rapidly increases through the primary winding of pulse transformer T701, and a resultant secondary pulse triggers thyristor Q701 into a conducting state. When thyristor Q701 is turned on, capacitor C702 discharges through the diodes 1-F and through the patient's body. As capacitor C702 discharges, the current through thyristor Q701 decreases until the minimum holding current is reached. At this point, thyristor Q701 turns off, and capacitor C702 begins recharging. Another pacing pulse will occur after 0.85 seconds unless spontaneous heart beat takes place. The diodes 1-F are employed for decoupling the pacer when no output pulse is provided therefrom. Also, inasmuch as the pacer output will generally be applied in parallel with defibrillator output terminals, the diodes prevent application of a defibrillator pulse to the pacer. The terminals 74 may be connected respectively to the electrodes 4 and 5 in FIG. 1 in the instance where the separate stimulating pulse electrodes are used, or alternatively to electrodes 1 and 3 in FIG. 1 when the same electrodes are being utilized for both deriving the electrical input from the patient and applying electrical stimulation to the patient. The pacer circuit is substantially similar to the pacer circuit described in the application of Warren S. Welborn and Melvin A. Holznagel, Ser. No. 66,189 filed Aug. 24, 1970, entitled "Cardiac Resuscitator", now U.S. Pat. No. 3,716,059.

Referring to FIG. 13, illustrating a defibrillator circuit, the output from nor-gate U8 in FIG. 7 is applied as the lower input of nor-gate U13 which, together with nor-gate U12, forms a flip-flop. When the output from gate U8 in FIG. 7 is thus applied, indicating the need for a defibrillating pulse, the output of gate U13 goes down and the output of gate U12 goes up. The output from nor-gate U12 is applied via inverter U82 for supplying a negative-going input to one-shot multivibrator 8-A which is substantially similar in construction and operation to one-shot multivibrator 7-C in FIG. 12. The resulting output pulse is applied to transistor Q801 for initiating a defibrillating output as hereinafter more fully described. A timing circuit including unijunction transistor Q803 is adapted for reverting the flip-flop U12, U13 after a predetermined period of time, i.e., several seconds, as set by potentiometer R803. Since the output of nor-gate U12 is normally low, capacitor C803 is normally substantially discharged, and unijunction transistor Q803 is inoperative. When the output of nor-gate U12 goes high, diode D805 becomes nonconductive and capacitor C803 starts charging. When the capacitor charges to a predetermined voltage, unijunction transistor Q803 discharges the same and provides a pulse output at the lower base of the unijunction transistor for application to the noninverting input of amplifier U17. The output of amplifier U17 is applied as input to nor-gate U12 for causing the output thereof to go low, and the flip-flop will be reset if the input of gate U13 from gate U8 in FIG. 7 has dropped. If such input from FIG. 7 has not disappeared, whereby another defibrillating pulse is apparently needed, the output of U12 will go high again when the output of amplifier U17 concludes. As a consequence, one-shot multivibrator 8-A will be triggered once more. As mentioned, the timing between outputs from one-shot multivibrator 8-A is determined by the setting of potentiometer R803. The output of one-shot multivibrator 8-A is further supplied as an input to counter U84 which functions to lock out the defibrillating circuit by supplying a positive level output to nor-gate U12 after a predetermined number of defibrillating pulses. Thus defibrillating pulses are not applied indefinitely if the patient is nonresponsive thereto. Counter U84 can be manually reset if desired by means of a circuit comprising switch S801, capacitor C803, capacitor C807 and diode D806. Capacitor C805 is normally charged toward a positive voltage, and upon depression of switch S801, this capacitor discharges through the switch and through capacitor C807, developing a positive input at inverter U86. Diode D806 prevents the input to U86 from dropping substantially below ground level. Inverter U86 inverts the positive input provided and resets the counter. A similar manual resetting circuit can be employed to reset counter U78 in FIG. 12 if desired.

In addition, the output of one-shot multivibrator 8-A is inverted and supplied as an input to or-gate 3-J used for clamping or gating off various detecting circuits during a defibrillating or pacing pulse. For example, the output of gate 3-J is suitably applied at 70 in FIG. 6. It further supplies the gating pulse at the lower input of nor-gate U63 in FIG. 10, and the lower input of nor-gate U73 in FIG. 11 as well as the upper gating input to or-gate U43 in FIG. 9. In the case of the lower gating input to gate U63 in FIG. 10, for example, the gating signal prevents the one-shot multivibrator U62, U63 from being triggered at this time.

Transistor Q801 in FIG. 13 has the operating coil of a relay K801 serially connected in its collector circuit. The contacts of relay K801 normally connect capacitor C801 to the output of a bridge circuit comprising diodes D801, D802, D803 and D804, receiving a high voltage alternating current input, for example from a high voltage power supply built into the means 24. However when transistor Q801 conducts, relay K801 connects capacitor C801, theretofore charged through the aforementioned bridge circuit, to terminals 72 via inductance L801, and diodes 1-E. Terminals 72 are suitably connected to the same terminals to which the aforementioned terminals 74 are connected for application of a defibrillating pulse to the patient. Capacitor C801, initially charged to the high voltage from the power supply, supplies this high voltage across the circuit comprising inductance L801, the switching diodes 1-E, and the body resistance of the patient. Inductance L801 controls the resulting current. Another defibrillating pulse cannot be applied to the patient until the circuit including elements R803, C803 and Q803 times out, and another defibrillating pulse is called for.

The diodes 1-E have the same purpose as the diodes 1-F hereinbefore mentioned. That is, the diodes 1-E and 1-F essentially decouple the pulse generators when either provides an output pulse. Application of a defibrillator pulse to the pacer or a pacer pulse to the fibrillator is prevented, as well as loading of the input circuitry, should the same electrodes be employed for the EKG input signal as for application of the stimulating output pulses. The defibrillator circuitry described above is similar to that described in the aforementioned U.S. Pat. No. 3,716,059.

In general, with the airway and electrode arrangement as illustrated in FIGS. 1 through 3, and with the electrical activity detecting circuits of FIG. 6, with the means of sensing bodily movement by audible indication of FIG. 10, with the logic circuit of FIG. 7, and with the pacer and defibrillator circuits of FIGS. 12 and 13 intercoupled as described, an electrical input detected at terminals 1, 2 and 3 in FIG. 6 for a requisite period of time will provide one logical input at terminal 54 in FIG. 7. Assuming an audible indication is also present for registering bodily movement, e.g., as indicating respiration, a second input to the FIG. 7 circuit will be provided at terminal 56. Consequently, neither the output of gate U8 nor the output of gate U9 will be up. (Also, neither would be up if respiration were detected in any case.) For other input combinations set forth in Table I, either the defibrillating pulse or the pacing pulse will be supplied. If a regular pacing pulse is supplied and heart action resumes between pacing pulses, the pacer of FIG. 12 will be disabled. If a defibrillating pulse is applied, a time period of several seconds elapses before the logical output of gate U8 is ascertained again, and if the need of a defibrillation pulse is again indicated, a further defibrillating pulse is applied. However, a limited number of defibrillating pulses, as counted by counter U84, will be applied to a patient before the counter shuts off the defibrillator circuit. As mentioned, the same electrodes may be used for both input of electrical activity information and output of stimulating pacing and defibrillating pulses, or separate electrodes may be utilized. The electrodes separately indicated in FIGS. 4 and 5 may be employed instead of or in conjunction with the electrodes on the airway. However, an electrode or electrodes on an airway together with an external electrode means such as electrode means 5 have been found in practice to provide the most satisfactory input in reelectrical activity information. Other indications of bodily movement may be inputted to or-gate U64, as indicated at reference numerals 58 in FIG. 10, so that a defibrillating pulse will not be applied to the patient in the presence of some other life-sign-indicating bodily motion. For instance, the strain gauge means 28 or 48 of FIGS. 4 or 5 may be connected as hereinafter described to provide such additional life sign indication.

Figure 9:
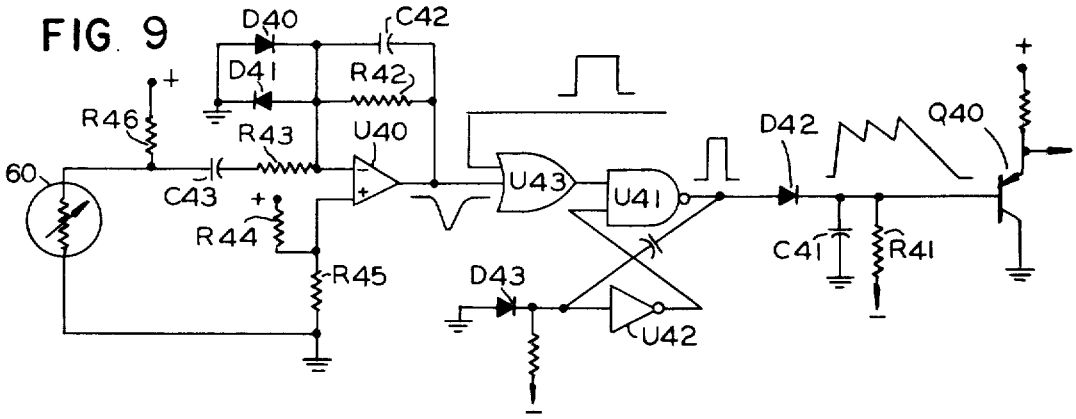
FIG. 9 is a schematic diagram of a circuit responsive to a mechanical transducer for indicating bodily movement in the case, for example, of respiration.

Referring to FIG. 9, a variable resistance 60 may, for example, comprise such strain gauge 28 of FIG. 4 or 48 of FIG. 5. The variable resistance may alternatively comprise a thermistor element or thermocouple element responsive to the cooling and/or heating effects of the patient's breath. Such element is suitably substituted for the microphone at the end of the airway, having substantially the same appearance as illustrated at 22 in FIG. 1. A current is supplied to element 60 via resistor R46 from a source of voltage. The junction between elements 60 and R46 is coupled via capacitor C43 and resistor R43 in series to the inverting input of amplifier U40, the latter being shunted in feedback relation by the parallel combination of capacitor C42 and resistor R42. A pair of reverse connected diodes D40 and D41 are disposed between the inverting input of amplifier U40 and ground for protection purposes. The noninverting input of amplifier U40 is connected to the midpoint of a voltage divider comprising resistors R44 and R45 disposed between a positive terminal and ground, while the output of amplifier U40 is applied as a first input to or-gate U43, the remaining or gating input therefor being derived from gate 3-J in FIG. 13 such that the output of gate U43 will be high during the defibrillator or pacing pulse application when there is likely to be patient movement caused by such impulse.

During motion of the chest, for example, during respiration, a negative-going output will periodically appear from amplifier U40 causing the output of gate U43 to drop. The output of gate U43 is applied to a monostable multivibrator comprising nor-gate U41 and inverting amplifier U42 connected in a conventional feedback manner. Diode D43, connected to the input, prevents that input from dropping substantially below ground level. When the negative going input is applied to gate U41, the output thereof goes positive for a predetermined period of time, and the positive pulses representing, for example, normal respiration are applied through detecting diode D42 to the ungrounded end of capacitor C41. The junction of the diode and the capacitor is returned to a negative voltage with the resistor R41. The time constant of the circuit is such that chest motion or the like must occur at least once every 30 seconds for the output as integrated by capacitor C41 to cause a continued high level output from transistor Q40. The emitter output of transistor Q40 is suitably applied as one of the inputs 58 of or-gate U64 in FIG. 10, thus providing this additional input indicative of bodily motion. The FIG. 8 circuit, connected to a strain gauge such as indicated at 28 or 48, may alternatively be substituted for the remainder of the FIG. 10 circuit if desired, thus indicating the presence of bodily motion to the logic circuit of FIG. 7 via gate U64. While a strain gauge indicative of chest movement associated with respiration has been discussed, such strain gauge or other similar device may be employed to detect other bodily motion in order to prevent application of the defibrillating pulse in the presence of such motion.

Figure 11:
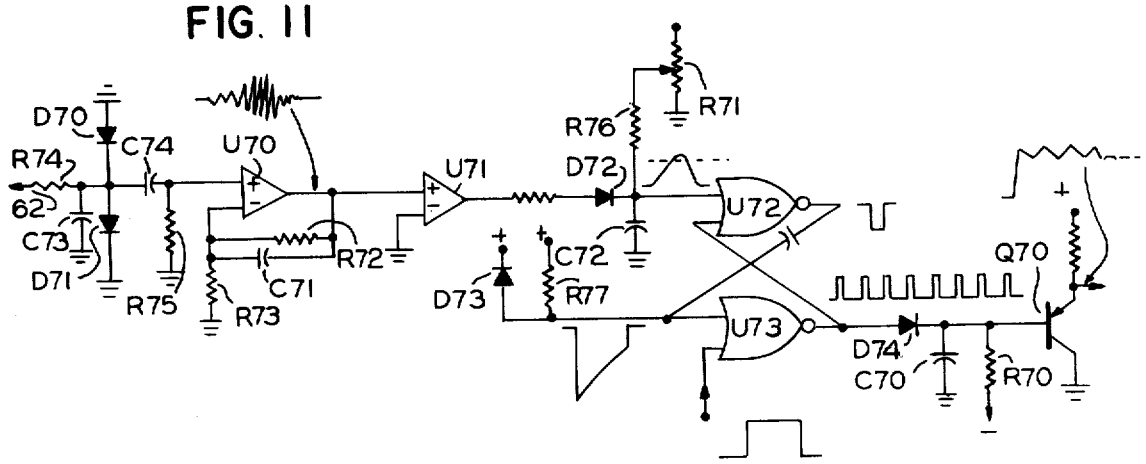
FIG. 11 is a schematic diagram of a circuit responsive to bodily movement in the form of blood flow sounds.

Referring to FIG. 11, an additional circuit is illustrated for detecting the sound of blood flow, e.g., near a constricted or bifurcated blood vessel, as a form of bodily motion sensing. A microphone or sound transducer positioned exteriorly of the blood vessel to detect such motion is coupled at 62 through the series combination of resistor R74 and capacitor C74 to the inverting input of amplifier U70, while the junction between elements R74 and C74 is returned to ground via capacitor C73 and the combination of reversely poled diodes D70 and D71. A resistor R75 returns the positive input of the amplifier to ground, and a feedback circuit comprising the parallel combination of capacitor C71 and resistor R72 is disposed between the amplifier output and the negative or inverting input of amplifier U70, the latter being returned to ground through resistor R73. The microphone connected at terminal 62 may comprise the same microphone 22, illustrated in FIG. 10, mounted on the end of the airway 10 in FIG. 1, but preferably comprises a microphone more suitably mounted, e.g., on the neck of the patient in such a manner as to detect the sound of turbulence of blood flow in the carotid system. Elements R74, C73, C74, R72 and C71 comprise a bandpass filter adapted to detect the characteristic sound of blood flow with each heart beat, as opposed to the actual heart beat sound itself, thus providing an additional or alternative parameter or means for sensing motion within the body as a life sign.

The output of amplifier U70 is applied to the non-inverting input of amplifier U71, the latter comprising a limiting and detecting amplifier operating as a zero crossing detector. The output of amplifier U71 is applied through diode D72 to an input terminal of nor-gate U72 and shunted to ground by means of capacitor C72. The same terminal is coupled through resistor R76 to a potentiometer R71. Components D72, C72, R76 and R71 operate as a threshold detector wherein a threshold level is established by the setting of potentiometer R71. Short duration artifact signals and the like will not charge detector capacitor C72 sufficiently for providing an operating input to nor-gate U72. Nor-gates U72 and U73 form a monostable multivibrator, cross-connected in the usual manner, employed to normalize the pulse duration. The feedback input of nor-gate U73 is returned to a positive voltage via the parallel combination of resistor R77 and clamping diode D73 which prevents the said input from rising materially above such voltage. The lower input of nor-gate U73 is supplied the gating signal output of or-gate 3-J in FIG. 13 for inhibiting operation upon the occurrence of a pacing pulse or defibrillating pulse.

Upon the occurrence of an input exceeding the threshold established for operating gate U72, indicative of the detected blood flow signals, the output of nor-gate U72 will go down and the output of nor-gate U73 will go up, a plurality of such positive-going pulses being generated at the output of nor-gate U73 indicative of the patient's pulse. The pulse output of nor-gate U73 is applied through detecting diode D74 to the ungrounded end of integrating capacitor C70, with the junction between these two components being returned to the negative voltage via resistor R70. Such junction is also connected to the base of transistor Q70, the emitter of which is suitably coupled to one of the inputs 58 of or-gate U64 in FIG. 10. Resistor R70 and capacitor C70 form a minimum acceptable pulse rate circuit wherein a pulse rate of 20 to 30 pulses per minute is required to provide a sufficient output for supplying an operative input to or-gate U64.

Figure 8:
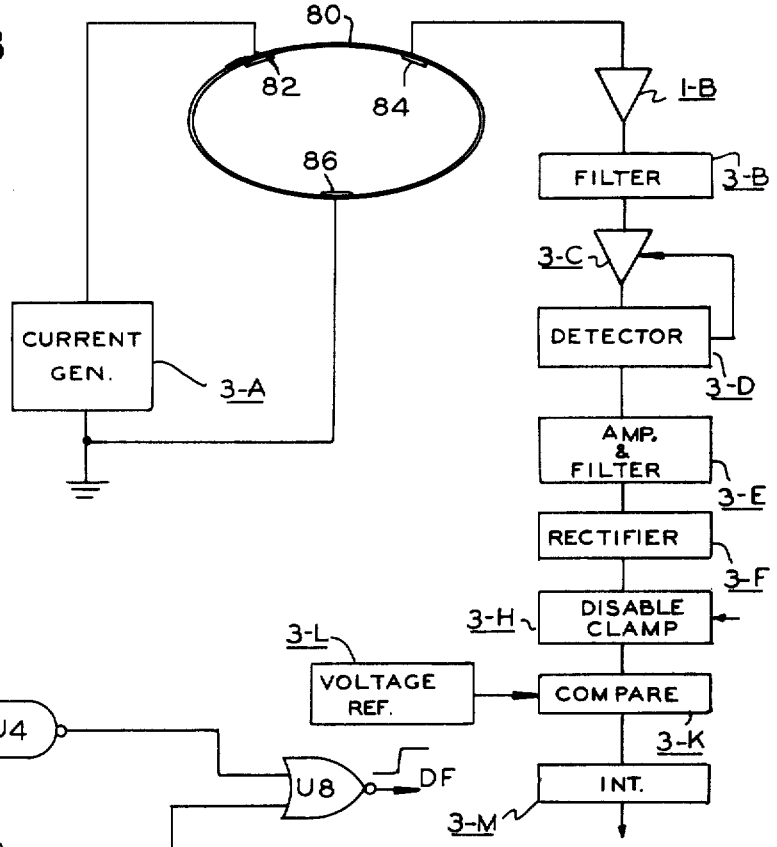
FIG. 8 is a schematic and block diagram representation of apparatus for determining bodily motion by means of impedance changes in the body according to a patient's pulse.

FIG. 8 illustrates further apparatus for detecting bodily motion, and in this case, for detecting mechanical movement in the patient's body indicative of the patient's heart beat. The apparatus includes a belt 80 of elastic material suitably disposed about the chest of the patient and provided with electrodes 82, 84 and 86. According to the FIG. 8 apparatus, a means comprising a current generator 3-A is employed for applying a signal to the patient, i.e., between electrodes 82 and 86, and further means is supplied for detecting a change in voltage drop at electrode 84 with respect to ground in response to changes in body impedance caused by mechanical heart activity or heart beat. The current generator 3-A may comprise a direct current generator for providing a D.C. current to the body, but preferably a fairly high frequency alternating current is utilized. Thus, current generator 3-A may supply an alternating current of constant amplitude at a frequency of approximately 100 kilohertz to the patient electrode 82 with respect to ground.

Changes in the electrical impedance of the body caused by the beating of the heart are detected by detecting changes in the high frequency component of the signal at electrode 84 as amplified by amplifier 1-B. The output of this amplifier is applied to high frequency bandpass filter 3-B which suitably rejects signals except those near 100 kilohertz. The output of filter 3-B is amplified by a further high frequency amplifier 3-D which has provision for automatic gain control. The output of circuit 3-C is applied to an A.M. detector (and A.G.C. unit) 3-D which provides a low frequency output to amplifier and filter unit 3-E, proportional to the changes in electrical impedance appearing in the patient's body. The amplifier and filter 3-E amplifies the desired signal component while attenuating unwanted components. In particular, low frequency signals, due in this case to patient respiration, may be attenuated. The output of circuit 3-E is applied to rectifier 3-F which produces output pulses of a single polarity. Disable clamp 3-H operates to inhibit transmission of the signal during delivery of electrical stimulation to the patient, this additional input being provided from gate 3-J in FIG. 13. The pulses from circuit 3-H are applied to comparator 3-K which supplies an output when such pulses exceed a voltage reference 3-L. Thus, a pulse occurs at the output of compare circuit 3-K whenever a rapid change in the patient's body impedance occurs. These pulses are then applied to integrator 3-M which in turn supplies an output when the pulse rate thus derived is in excess of a predetermined value between 20 and 30 pulses per minute. The integrator circuit may be constructed in a substantially similar manner to the integrating circuits hereinbefore disclosed, and the remainder of the circuit is substantially similar to the "I.C.G." circuit as set forth and claimed in the hereinbefore mentioned U.S. Pat. No. 3,716,059. The output of integrator 3-M is suitably coupled as an additional input, 58, to or-gate U64 in FIG. 10.

The apparatus according to the FIG. 8 circuit is described above in connection with measuring the patient's pulse by means of measuring impedance changes substantially across the patient's chest, detected at a rate generally associated with a normal pulse range. In accordance with the present invention, the circuit constants of amplifier and filter 3-E are readily altered so that the FIG. 8 apparatus is specifically responsive to the patient's respiration as a life sign, instead of or in combination with the above described response relative to the patient's pulse. In any case, the output of the circuit is applicable as an additional input to or-gate U64 as mentioned.

Apparatus according to the present invention may also include a continuity checker which determines if the patient electrodes are in proper electrical contact with the patient's body, with particular reference to the electrodes employed in deriving the EKG signal, i.e., electrodes 1, 2 and 3. If poor contact is made, defibrillator and pacer output is inhibited. A current is suitably applied to electrodes 1 and 2 with respect to electrode 3 and the resulting voltage at electrodes 1 and 2 with respect to 3 is measured. If an electrode is in poor contact with the patient, a comparatively high voltage will occur at that electrode and such voltage will be sensed for inhibiting operation of the apparatus. A type of continuity interface unit is set forth in the aforementioned U.S. Pat. No. 3,716,059. However, rather than a DC source, an AC source having an operating frequency of approximately 100 KHz is preferred in the case of equipment according to the present invention, whereby an AC voltage drop at that frequency is sensed for checking continuity. As hereinbefore indicated, when airway mounted EKG electrodes are employed, the danger of lack of continuity is minimized. However, the continuity circuit may be added.

It is not implied that each of the bodily motion detecting means hereinbefore disclosed will necessarily be utilized in a single apparatus, but these circuits and devices are disclosed as suitable alternatives in the detection of bodily motion as a life sign parameter. In a given instance, the airway of FIGS. 1 through 3 may alone be employed for deriving both the electrical and respiratory sound motion inputs, and for providing stimulating pulse outputs on electrodes thereof in conjunction with the attendant circuitry apparatus of means 24 as hereinbefore described. The additional electrode means 5, as an electrical input electrode and as a stimulating pulse application return, is also suitably employed as illustrated in FIG. 1. In the case of such apparatus, additional means comprising a belt or similar attachment as illustrated in FIGS. 4, 5 and 8 may be applied to the patient, especially if these attachments can be connected to the patient without undue delay. In the latter instance, then, additional inputs are supplied via or-gate U62. Alternatively, a belt, tongs, or similar means can be employed in a manner hereinbefore described either in conjunction with the airway or alone for ascertaining both electrical activity and bodily movement, and for supplying a stimulating output to the patient in accordance with Table I.

In general, the apparatus is applied to the suspected heart attack adult patient, with a power supply appropriately energized, for making the input measurements and supplying outputs, e.g. in accordance with Table I. If substantial cardiac arrest has occurred, indicated by a very slow or nonexistent pulse, a pacing stimulation is applied to the patient. If, on the other hand, substantial electrical activity is present, while one of the forms of bodily motion such as respiration is absent, ventricular fibrillation is indicated, and a defibrillating pulse is applied to the patient. The defibrillating pulses are well separated by a period of several seconds, with the condition of the patient being re-ascertained before another defibrillating pulse is applied.

Since corrective action may be taken by the resuscitator as soon as or even before an ambulance team of first aid personnel has reached the patient, the chances for survival are materially increased as compared with the chances of survival when treatment must await transport of a heart patient to a hospital.

Figure 14:
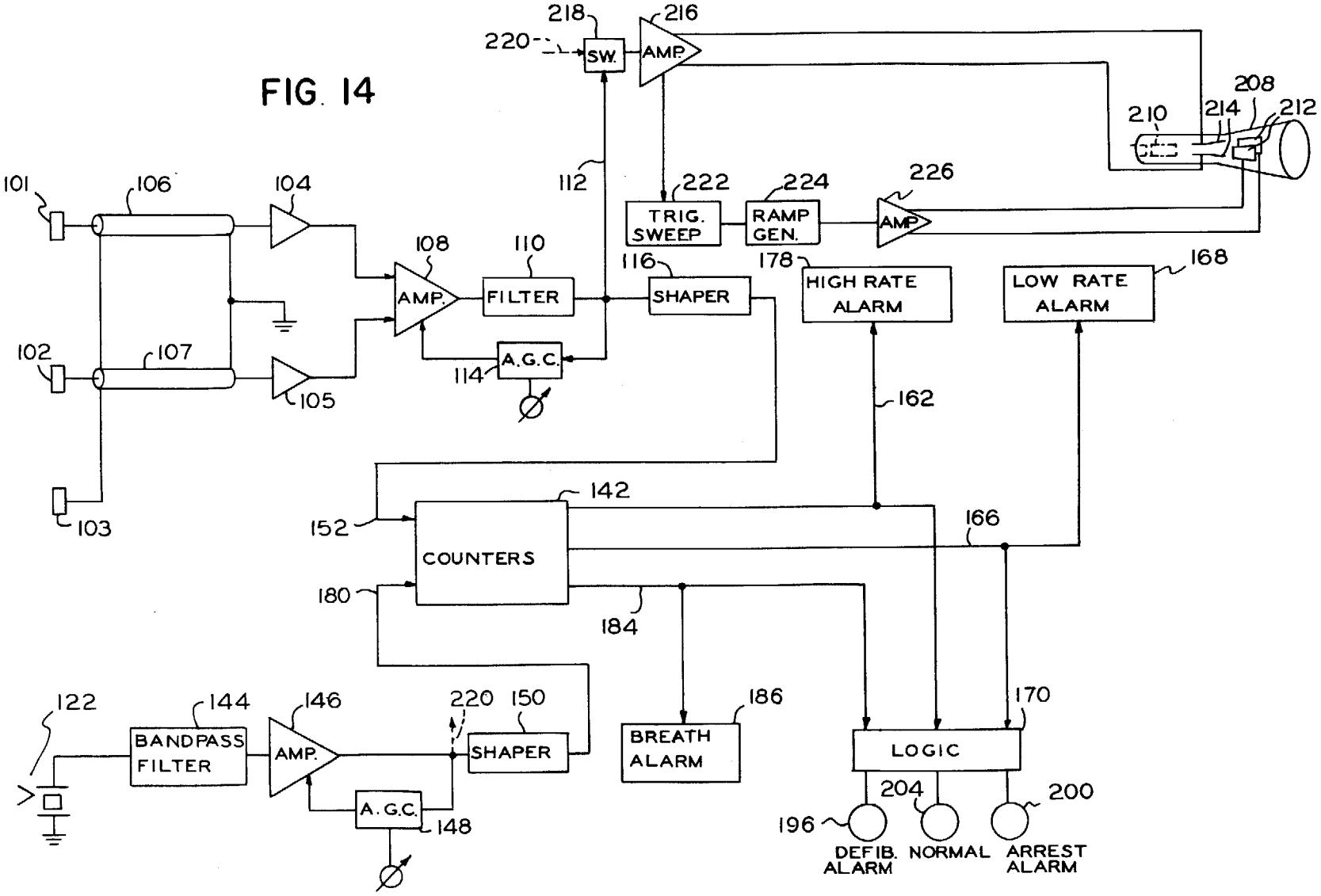
FIG. 14 is a schematic and block diagram of a circuit connectable to patient-contacting electrodes for providing output signals indicative of patient electrical heart activity, said circuit further including apparatus for providing signals indicative of patient respiration and for making a logical determination of the patient's condition.

FIG. 14 illustrates alternative monitoring circuitry suitably employed for providing a life sign monitoring output, indicative of normal heart action, cardiac arrest or fibrillation. The input is provided on terminals 101, 102 and 103 which may correspond to terminals 1, 2 and 3 in the FIG. 6 circuit, and which may be similarly connected to patient contacting electrodes such as those mounted on airway 10 and electrode means 5. The input portions of the circuit of FIG. 14 are also suitably similar to those illustrated in FIG. 6. However, protective elements for preventing damage to the circuit from pacing and defibrillating pulses need not be employed if a pacer or defibrillator is not connected at the same time to the patient or to the same patient contacting electrodes. The FIG. 14 circuit is shown in simplified form, it being understood that various coupling components, feedback elements, etc., may be included which are substantially similar to those as illustrated in the FIG. 6 embodiment. The FIG. 14 embodiment has the advantage of more closely measuring the patient's pulse rate, and respiration rate, to determine if they are within predetermined limits. A numerical output may be provided.

Terminals 101 and 102 are respectively connected to inputs of isolation amplifiers 104 and 105 through coaxial cables 106 and 107, the exterior conductors of which are grounded and connected to electrode 103. The outputs of amplifiers 104 and 105 are coupled to inverting and noninverting inputs of differential amplifier 108 the output of which drives band pass filter 110 employed to reduce the effects of muscle potentials and external interference. The low frequency band limit of filter 110 is suitably 3 Hertz, while the high frequency cutoff is suitably set to approximately 50 Hertz. The output of the filter may be presented on lead 112 for application to means for providing an electrocardiogram as hereinafter described. Lead 112 is also connected to the input of automatic gain control circuit 114 which applies feedback to amplifier 103 for the purpose of presenting electrocardiogram outputs within predetermined limits.

Figure 17:
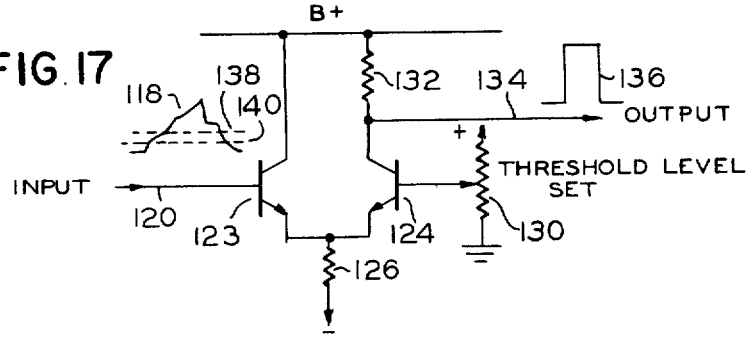
FIG. 17 is a schematic diagram of a shaper circuit as employed in the FIG. 14 apparatus.

The output of filter 110 is also applied to shaper 116 which is illustrated more fully in FIG. 17 and which may be defined as a threshold detector and regenerator providing a standard output pulse for each valid input signal.

Referring to FIG. 17, an input signal 118 is presented on lead 120 connected to the base of a first NPN transistor 123 having its emitter coupled in common with the emitter of NPN transistor 124 to a negative voltage terminal through resistor 126. The base of transistor 124 is coupled to the movable tap of a potentiometer 130 the end terminals of which are connected to a positive voltage and ground. The collector of transistor 122 is connected to a B+ voltage, and the collector of transistor 124 is returned to B+ through load resistor 132 as well as being connected to output lead 134 where square wave output 136 is supplied. The circuit is characterized by input hysteresis limits 138 and 140 which are relatively close in voltage value such that the circuit turns on and produces a positive-going output on lead 134 when the input crosses level 138 in a positive-going direction, while providing a negative-going output on lead 134 when the input crosses level 140 in a negative-going direction. The input levels ae substantially selected by potentiometer 130 such that square wave output 136 is indicative of a valid heart beat. This pulse is provided as a first input to counters 142 in FIG. 14.

The FIG. 14 circuit also suitably receives an input from microphone 122 which may be mounted upon an airway or the like, corresponding to microphone 22 in FIG. 10. One terminal of the microphone is grounded and the remaining terminal is coupled through band pass filter 144 to amplifier 146. The microphone is employed for ascertaining bodily movement or physical activity, and in particular for ascertaining respiration sound, whereby the filter 144 is suitably arranged to have an upper band limit of approximately 700 Hertz and a lower band limit of approximately 100 Hertz appropriate for passing breath sound frequencies.

Amplifier 146 is further provided with an automatic gain control circuit 148 and also drives a shaper 150 which may have the same circuit configuration as described in connection with FIG. 17. The output of shaper 150 is coupled to counters 142.

Figure 15:
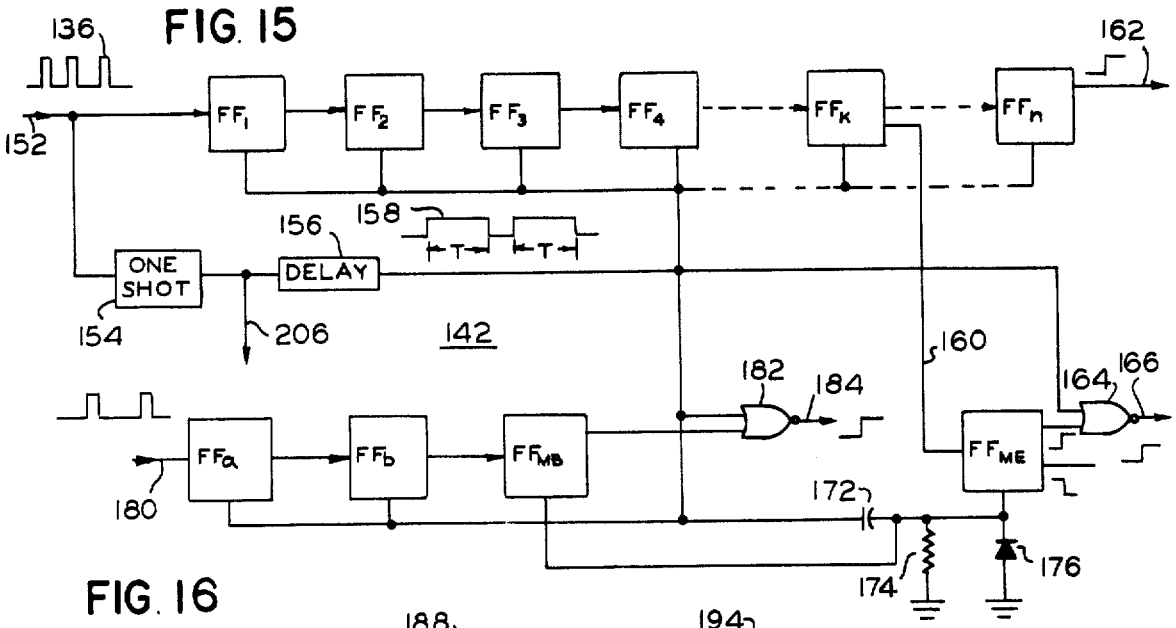
FIGS. 15 and 16 are schematic and block diagrams further illustrating logical circuitry for providing an indication of the patient's condition.

Counter circuitry 142 is further illustrated in FIG. 15 wherein the output from shaper 116 in FIG. 14 is received on lead 152 and comprises a plurality of pulses 136, one for each heart beat of the patient. This input is applied to first counter flip-flop $FF_1$, as well as to one-shot multivibrator 154 the output of which is delayed by delay line 156 and appears as a series of "stretched" pulses 158 each having a duration T. A given pulse 136 changes the state of one-shot multivibrator 154 from its stable condition to its unstable condition for producing the output pulse having a duration, T, corresponding to the normal total period of several input pulses 136 as will hereinafter be appreciated. The same pulse which triggered one-shot multivibrator 154 will also trigger flip-flop $FF_1$ from a first state to a second state while the next input pulse 136 in order will trigger flip-flop $FF_1$ from the second state back to the first state. Coincident with the last transition, flip-flop $FF_1$ will trigger flip-flop $FF_2$ from its first state to a second state. Flip-flop $FF_3$ is triggered from $FF_2$, while flip-flop $FF_4$ is triggered from flip-flop $FF_3$, and so on in binary counter fashion. Flip-flop $FF_k$ is selected to provide an output indicative of the minimum acceptable heart rate by providing an output on lead 160 during a period, T, before the flip-flop is reset. Also, a flip-flop $FF_n$ provides an output on lead 162 indicative of an excessively high heart rate when flip-flop $FF_n$ is triggered within the period, T, before being reset. All the flip-flops, $FF_1 \ldots FF_n$, are reset at the trailing edge of each pulse 158. As will be appreciated by those skilled in the art, the length of the period, T, and the number of flip-flops, $FF_1 \ldots FF_n$, are chosen such that the number of pulses k divided by time, T, is descriptive of a minimum acceptable heart rate, while the number of pulses n divided by time T is indicative of an excessively high heart rate, wherein k and n are the number of pulses 136 required to operate flip-flops $FF_k$ and $FF_n$ respectively. The dashed lines in FIG. 15 indicate additional flip-flops as may be employed to satisfy those criteria.

When flip-flop $FF_k$ changes states, the output on lead 160 triggers memory flip-flop $FF_{ME}$ whereby the same provides one input to nor-gate 164. The other input for nor-gate 164 is provided from delay line 156, so that at the end of a time T, i.e. during the lock out period between pulses 158, nor-gate 164 will provide a positive output on lead 166 if memory flip-flop $FF_{ME}$ has not been triggered from flip-flop $FF_k$ in the meantime. The output on lead 166 is suitably applied for operating low rate alarm 168 in FIG. 14 and is also connected to logic circuitry 170. The low rate alarm is suitably a warning light, an audible tone emitting device, or the like.

Memory flip-flop $FF_{ME}$ is subsequently reset, at the beginning of the next pulse 158, via a differentiating circuit comprising capacitor 172 interposed between delay line 156 and the reset terminal of flip-flop $FF_{ME}$, such differentiating circuit also including a resistor 174 disposed between such terminal and ground. The resistor is shunted by a diode 176 having its cathode grounded such that flip-flop $FF_{ME}$ is receptive only to a positive-going reset input provided at the beginning of each pulse 158. If the counter chain $FF_1 \ldots FF_n$ counts out and provides an output on lead 162, indicating an excessively high heart rate, high rate alarm 178 in FIG. 14 will be actuated, the same constituting a warning light, audible tone emitting device, or the like. The output on lead 162 is also applied to logic circuitry 170.

The remaining input to the FIG. 15 circuit is provided on lead 180 and is derived from shaper 150 in FIG. 14. The input on lead 180 comprises a series of pulses each indicative of a respiration sound, the pulses being coupled to a first flip-flop $FF_a$ which in turn is coupled to trigger flip-flop $FF_b$. Although two such flip-flops are shown for purposes of illustration, it will be understood the number of such flip-flops will be chosen such that flip-flop $FF_b$ will be triggered and provide an output if the pulse input on lead 180 indicates a minimum standard of respiration during a period, T. If such minimum standard is attained, memory flip-flop $FF_{MB}$ will be triggered and provide a first output to nor-gate 182. The remaining input to gate 182 is supplied from delay line 156. Nor-gate 182 will provide a positive-going output on lead 184 only if flip-flop $FF_{MB}$ has not been triggered by the end of a pulse 158. Flip-flops $FF_a$ and $FF_b$ are reset at the lock out period between pulses 158. However, flip-flop $FF_{MB}$ will be reset at the beginning of the next pulse 158 coincidently with the resetting of flip-flop $FF_{ME}$. The output on lead 184 is applied to breath alarm 186 in FIG. 14 which may comprise a warning light, audible tone emitting device, or the like, as well as to logic circuitry 170. The lock out period between pulses 158 is brought about in response to the end of the unstable period of one-shot multivibrator 154. The next pulse 158 will be initiated in response to another input pulse 136 triggering one-shot multivibrator 154, thereby initiating another counting period.

Figure 16:
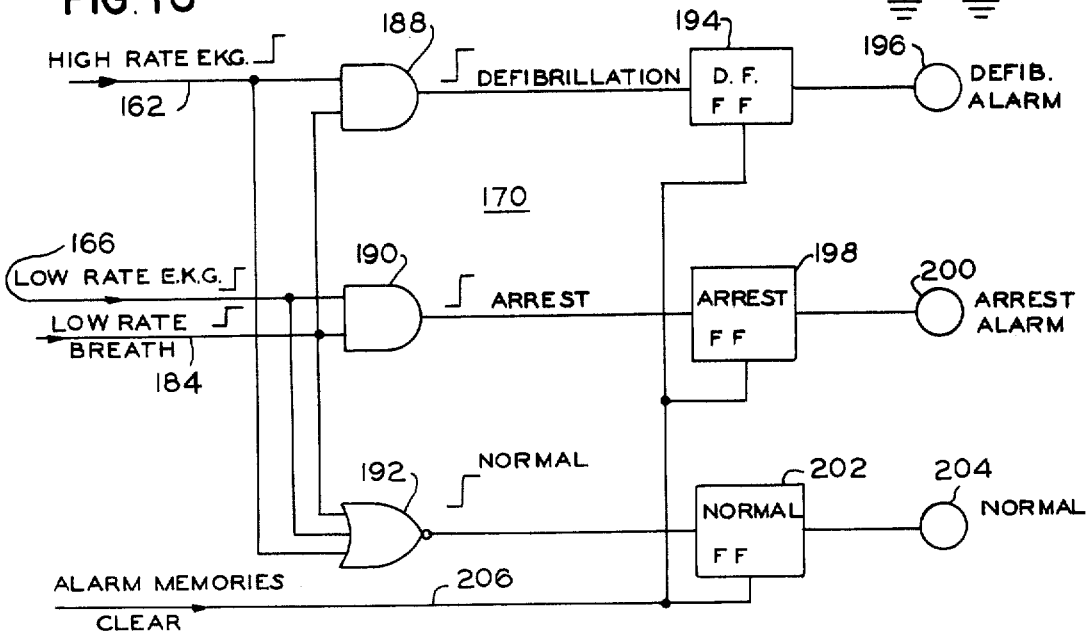

Logic circuitry 170 is more fully illustrated in FIG. 16 wherein inputs on lead 162 and 166 and 186 are variously applied to gates 188, 190 and 192. A positive-going input on lead 162 indicative of an abnormally high heart rate, together with a positive-going input on lead 184, indicative of an abnormally low breath rate, will operate and-gate 188 for triggering flip-flop 194. The latter then provides an operating output for defibrillation alarm 196 which may comprise a warning light, sound emitting device or the like.

A positive input on lead 166 indicative of an abnormally low heart rate together with a positive input on lead 186 indicative of an abnormally low breath rate will operate and-gate 190 for triggering flip-flop 198, the latter providing an input for operating arrest alarm 200 which may also comprise a warning light, sound emitting device or the like.

If the indications on all the input leads, 162, 166 and 186, are negative indicating normal behavior of the patient within set limits, nor-gate 192 will provide a positive output for setting flip-flop 202 which operates normal indicator 204 suitably comprising an indicating light. The flip-flops 194, 198 and 202 are reset each time one-shot multivibrator 154 resets itself, via one-shot multivibrator output lead 206. It will be observed that the flip-flops 194, 198 and 202 are reset slightly before the end of each pulse 158 provided at the output of delay line 156. Then, the outputs from the memory flip-flops of counter circuitry 142 will be supplied during the lock out interval between pulses 158 such that flip-flops 194, 198 or 202 will be set and this condition retained until slightly before the beginning of the next lock out interval. The delay of delay line 156 is arranged to be a fraction of the time period T. Although the circuitry of FIGS. 14, 15 and 16 is primarily described in connection with providing monitoring outputs, it will be appreciated that indications of defibrillation and arrest can alternatively be employed for operating a defibrillator or pacer of the general type hereinbefore described.

Returning to FIG. 14, apparatus may be employed for visually portraying the electrocardiogram and/or breath sounds or other indications of bodily movement. Such apparatus may comprise a cathode ray tube 208 having an electron gun 210, horizontal deflection plates 212, and vertical deflection plates 214. The vertical deflection plates are connected to receive push-pull outputs from vertical amplifier 216 which receives its input from electronic switch 218. Electronic switch 218 alternatively receives the output on lead 112 from filter 110, comprising the electrocardiogram signal, or a breath sound signal on lead 220 comprising the output of amplifier 146. The electrocardiogram and breath sound viewed by this means may be viewed in a superimposed manner, or adjacent one another on adjacent cathode ray tube traces under the control of switch 218 wherein amplifier 216 is a DC amplifier and electronic switch 218 adds different DC voltage levels to the respective signals as applied to the amplifier 216. A triggering signal level is also detected in amplifier 216 and applied to trigger shaper 222 which may be of the general type hereinbefore described in connection with FIG. 17 and employed for initiating operation of ramp generator 224. The latter provides a saw tooth signal to push-pull amplifier 226 driving the horizontal deflection plates 212 of cathode ray tube 208. The trigger circuitry operates for initiating periodic traces in response to ones of the electrocardiogram or breath signals, or the ramp generator may be operated at a relatively low and substantially independent frequency. In any case, the cathode ray tube traces are conventionally slow and cathode ray tube 208 is chosen for fairly high trace retention characteristics by selection of a phosphor having high image persistence.

Figure 18:
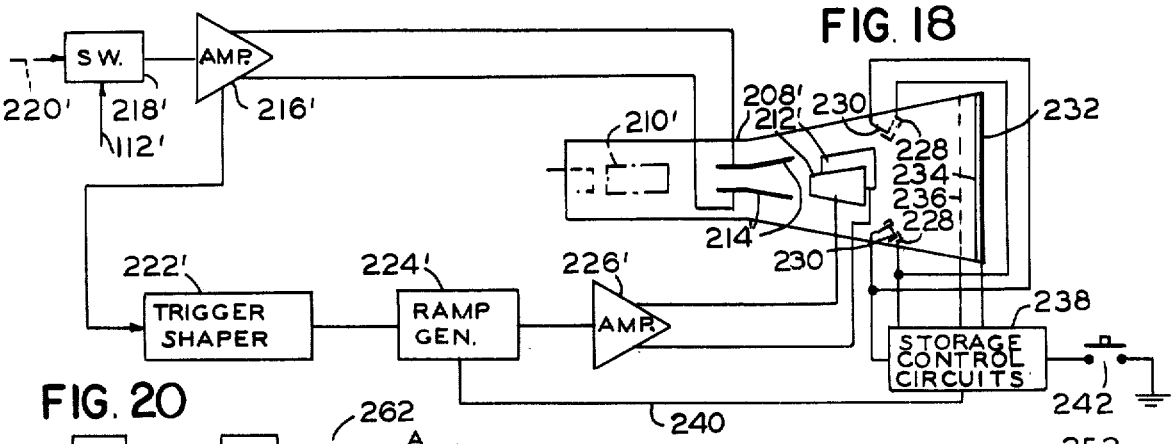
FIG. 18 is a schematic and block diagram of an alternative form of a portion of the FIG. 14 apparatus.

Alternatively, apparatus may be employed including a cathode ray storage tube for retaining one or more electrocardiogram traces or breath sound traces. This circuitry is illustrated in FIG. 18 wherein similar elements are referred to by means of primed reference numerals and only substantial differences from FIG. 14 apparatus will be described. The cathode ray tube 208' is further provided with flood guns each having an anode 228 and a cathode 230 for providing a flood of electrons directed toward a target comprising a transparent target electrode 232 disposed on the inside of the tube's face plate and covered by light emitting phosphor material 234. A storage mesh electrode 236 comprises a conductive mesh and a storage dielectric which has the faculty of storing a charge image written thereupon by the electron beam from electron gun 210', the charge image being written and held through the medium of secondary emission as well understood by those skilled in the art. Moreover, flood electrons from the flood guns are passed to the phosphor layer and target electrode in accordance with the stored image. As a result, an electrocardiogram or the like received via electronic switch 218' may be displaced and held as written, but may be erased at the end of each horizontal sweep when a signal indicating the end of such sweep is provided on lead 240 coupled from ramp generator 224' to storage control circuitry 238 from which the appropriate voltages for the flood gun elements, mesh and target electrode are normally applied. At the end of a horizontal sweep, the normal storage enabling voltages are altered whereby the stored image fades and a new electrocardiogram image is provided beginning with the next sweep. Alternatively, the electrocardiogram may be continuously stored on the same horizontal trace or several spaced horizontal traces until erased by means of push button 242. For spaced horizontal traces, switch 216' may be adapted to add a separate DC level to the input each time a new trace begins. Ramp generator 224' is then connected to electronic switch 218' by means not shown.

Figure 19:
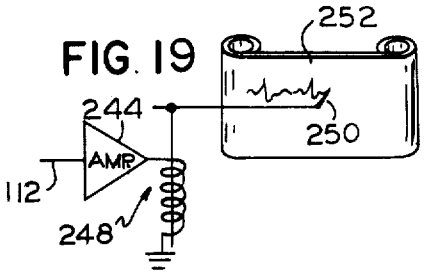
FIG. 19 is a schematic diagram of another alternative form of a portion of the FIG. 14 apparatus.

FIG. 19 illustrates schematically a mechanical electrocardiograph which may alternatively be employed in providing a permanent record of the signal supplied on lead 112 from filter 110 in FIG. 14. The signal is coupled to an amplifier 244 driving an electromagnetic device 248 which controls a linkage connected to stylus 250. Stylus 250 is controlled in a conventional manner for providing a written record of the signal on moving roll chart 252.

Figure 20:
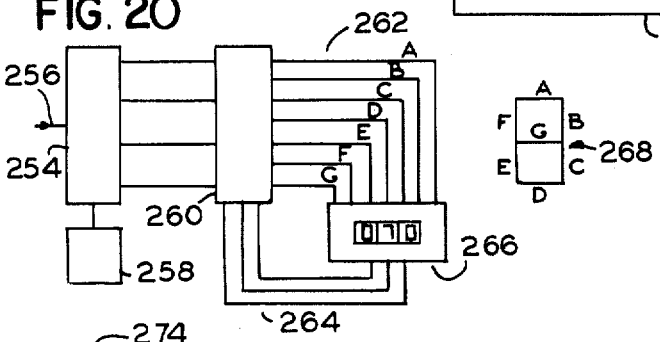
FIG. 20 is a block diagram of numerical readout circuitry which may be employed in conjunction with the FIG. 14 apparatus.

FIG. 20 illustrates alternative apparatus employed in conjunction with the apparatus of FIG. 14 for providing a numerical output indicative of the actual pulse rate or breath rate derived by means of the FIG. 14 apparatus and in particular utilizing the information from the counter circuitry 142 as illustrated in FIG. 15. An input lead 256 is coupled alternatively to lead 152 or 180. Counter and memory circuit 254 counts and remembers the number of heart beats or respiration signals received during a given interval, which interval is set by clock interval generator 258. The output of counter memory circuit 254 is suitably provided in binary coded decimal form to a decoder 260 for converting the binary coded decimal output to a seven segment output on leads 262, lettered A through G, coupled to display unit 266. Display unit 266 successively displays numerical representations in the style indicated at 268, i.e. composed of segments A through G corresponding to the ones of leads 262 energized from decoder 260 at a given time. Each numerical display is suitably a light-emitting display providing seven horizontal and vertical light-emitter segments which, if all energized, would provide a visible representation of the FIG. 8 in block style. The other numerals are formed from a lesser number of such segments.

Since more than one binary coded decimal digit will ordinarily be required for expressing the rate to be displayed, especially in the case of pulse rate, the individual digits thereof are successively selected by decoder 260 while at the same time energizing an appropriate one of the digit lines 264 for bringing about the gating on of one of three numerical displays in display unit 266. The numerical displays representative of the respective digits are repeatedly energized in order that a substantially constant output number is continuously displayed, unless, of course, the heart rate or breath rate being measured changes. A circuit as illustrated in FIG. 20 is suitably employed for providing a numerical pulse rate output, while another such circuit is suitably employed for supplying the numerical output indication of respiration rate.

Figure 21:
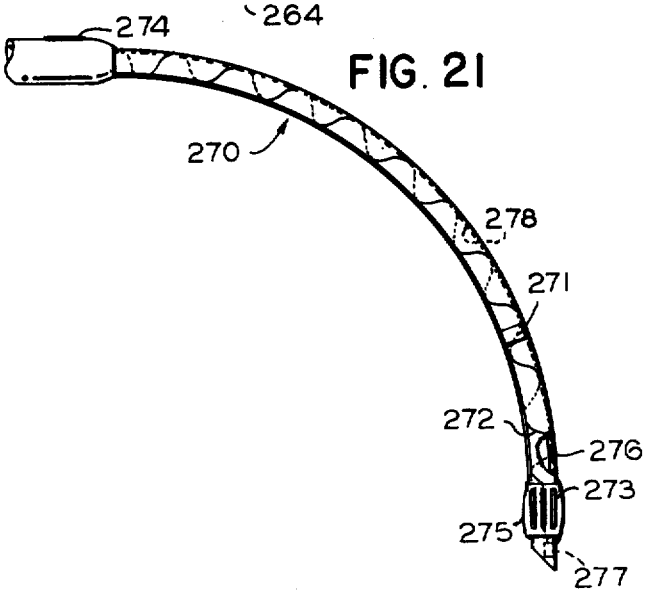
FIG. 21 is a side view of an intratracheal tube employed as a sensing device according to the present invention.

The circuitry herein described either for monitoring heart rate, providing EKG information, or supplying resuscitating impulses to the patient has been described in conjunction with the advantageously employed airway 10 of the type illustrated in FIG. 1 and the external electrode means of FIG. 1, or in conjunction with one of the chest-applied means as illustrated in FIGS. 4, 5 and 8. Alternatively, a plastic intratracheal tube 270 as illustrated in FIG. 21 is suitably provided with a conducting wire or ribbon 272 extending from an upper contact 274 down the length of the intratracheal tube. The wire or ribbon 272 may connect to electrode 271 mounted near the lower end of the tube and electrodes 273 mounted on expandable portion 275, as well as to end tip electrode 277, for making good electrical contact with the interior of the moist passage. The conducting wire or ribbon is desirably embedded in the surface of the intratracheal tube so that the upper conducting surface of such wire or ribbon is flush with the exterior of the tube to prevent damage when the tube is inserted or removed. The wire or ribbon 272 is in many cases advantageously helically disposed about the tube as illustrated for making contact with the body all the way along the tube, especially in the absence of contacts 271, 273 and 277. However, when contacts 271, 273 and/or 277 are employed, wire or ribbon 272 can be completely embedded within the plastic wall of the tube, and it is not necessary for the conducting wire or ribbon to be helically wound about the tube. The electrodes 271, 273 and 277 may then be positioned for obtaining an EKG input at a specified location or region within the body.

The contact 274 will be connected to terminal 1 in the FIG. 6 circuit or terminal 101 in the FIG. 14 circuit, while an external electrode means 5 including electrode 6 may be employed as an outside electrode for connection to terminals 2 or 102 in the FIGS. 6 and 14 circuits. The remaining or ground electrode may be attached elsewhere to the patient or to a conductive table upon which the patient rests. A microphone 276 is suitably carried by the intratracheal tube 270 and connects to the FIG. 10 and FIG. 14 apparatus via leads 278 in the manner hereinbefore described in the case of microphones 22 and 122. The microphone then provides audible input of breath sounds and the like. The intratracheal tube would not ordinarily be utilized in making initial contact with a patient having a suspected heart attack, but is a desirable input means to be employed in the case of a patient already requiring such intratracheal tube. The electrode connection and sound reproducing means provided can then be conveniently connected at will to the monitoring devices for ascertaining the patient's condition as hereinbefore described, and for providing emergency resuscitating impulses. In the latter case, the contact 274 may also be employed together with external electrode means such as electrode means 5 including electrode 6 for coupling pacing or defibrillating impulses to the patient.

Figure 22:
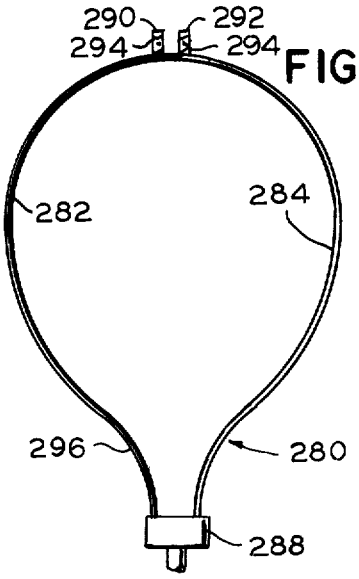
FIG. 22 is a view of a nasal tube employed as a sensing device according to the present invention.

FIG. 22 illustrates another airway type of device 280 comprising tubes 282 and 284 attached to connector 288 for supplying oxygen to the tubes. These tubes mount plastic nasal tubes 290 and 292 utilized for supplying oxygen to a patient and about which conducting wires or ribbons 294 are wound for making electrical contact with a patient. The conducting wire or ribbon is embedded such that the top surface thereof is substantially flush with the exterior of the tube, and such wire or ribbon is in each case connected to a conducting wire 296 employed for coupling to the circuits of FIGS. 6 or 14 for use in substantially the same manner as described for the FIG. 21 device, as well as to other previously described circuitry for providing pacing or defibrillating impulses.

Figure 23:
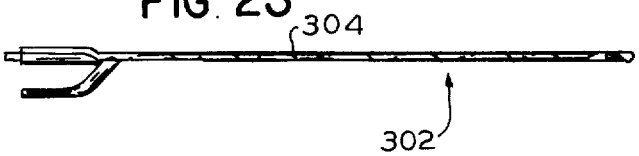
FIG. 23 is a side view of a catheter employed as a sensing device according to the present invention.

FIG. 23 illustrates a catheter 302 for insertion into a bodily opening in substitution for an airway or the like in the case of a patient already requiring a catheter. The catheter is provided with a helically wound wire or ribbon conductor 304 embedded in the surface thereof, wherein the exterior of the conductor is flush with the surface of the plastic catheter tube. Connection to external circuitry is made via conductor 304 in the manner hereinbefore described for an airway electrode for deriving electrical signals from the heart and providing resuscitating impulses.

In many cases, a monitoring system according to the present invention will be connected under emergency conditions to the patient by means including the airway 10 in FIG. 1, and the airway will be ejected by the patient when he regains consciousness, for example after resuscitation. However, it is then desired to substitute other connecting means to the patient for continuously monitoring his heart condition. When the airway is ejected, the device 306 illustrated in FIG. 24 may be substituted therefor. Such device is designed for at least partial insertion into or onto the body or passageway of a patient, e.g. the lip or mouth of the patient. The device comprises a bifurcated metal spring clip adapted for sliding onto the lip or cheek of the patient and includes opposed member portions 308 and 310 which are spring biased toward one another. The member portion 308, adapted for insertion within the mouth or cheek, suitably supports a microphone 314 employed for detecting breath sounds and suitably connected in the manner of microphones 22 or 122 in FIGS. 10 and 14. The device 306 is connected to the previously described circuitry by means of connecting lead 312 to the aforementioned terminals 1 or 101, and may also be utilized in the case of further emergency for applying pacing and defibrillating pulses if necessary.

Another device for attachment to the patient, after ejection of the airway, is illustrated in FIG. 25, the device being numbered 316. This device takes the form of a clamp including forward opposed member portions 318 which are normally spring biased toward one another by spring 320, the device further including levers 322 rearward of the spring and integral with member portions 318 by means of which the member portions 318 are forced apart for separating the same whereby the device may be inserted onto the lip or mouth. The member portions 318 are spaced apart rearward of their forward or contacting areas so that a relatively firm contact may be made with the moist tissue inside the lip or cheek. The device is suitably formed of conducting metal and is provided with a connecting lead 324 for coupling the device to the hereinbefore described apparatus for use in the same manner as indicated for the device of FIG. 24. The FIG. 25 device may also support a microphone for insertion within the mouth of the patient as previously mentioned in respect to the FIG. 24 device.

Utilization of a connection external to the patient has been hereinbefore described, for example, in particular regard to the electrode means 5 provided with electrodes 6 and 7. This electrode means, as illustrated in FIG. 1, is suitably employed in conjunction with means substituted for an airway as in the case of a conscious patient, as well as in conjunction with the airway itself, the electrode means 5 being placed elsewhere on the patient for example on the chest or abdomen area to provide an opposite polarity input signal electrode means or reference electrode means, as well as forming possible output electrode means. While suitable connection can be made with the patient by holding or strapping such electrode means 5 on the patient, alternative external electrode contacts as contemplated according to the present invention are preferred for providing a quicker and more certain electrical circuit connection. One such device, suitable for external connection, has already been described in connection with FIG. 25 and comprises a spring biased clamp. Such spring biased clamp may alternatively be attached to the patient at a location remote from the mouth, for example clamped on an extremity such as a finger, or clamped to a "flap" of skin which may be gathered between opposed member portions 318 or a "web" of skin as between the thumb and fingers or the like. The FIG. 25 clamp, employed in this way, is ordinarily utilized as the external connection in combination with an airway or similar device for providing the opposite polarity EKG terminal. Of course, in the event that the airway is ejected by the patient as hereinbefore mentioned, devices of the type illustrated in FIG. 25 may be employed both at the patient's mouth and at a location remote therefrom, such as in the chest or abdomen area, extremity, or the like.

Another similar device 326 is illustrated in FIG. 26 and comprises opposed metal clamping members 328 and 332, each respectively integral with one of a pair of rearward metal handle portions 334 and hingedly connected to one another. Spring 336 biases member 328 toward member 332, member 328 being slightly wider than member 332 and carrying a pair of relatively sharp contacts 330 at the forward end thereof which adjoin either side of member 332 when the members are closed toward one another. The device is designed for clamping to an extremity, flap of skin, or the like wherein the sharp contact means 330 are adapted to penetrate the patient's skin and reach the subcutaneous layer whereby a more certain electrical connection is made. An electrical lead 333 is supplied for connecting the device 326 to the hereinbefore described circuitry of FIGS. 6 or 14 in place of electrode means 5.

A further device which may be utilized for making external contact with the patient in place of the electrode means 5 is illustrated in FIGS. 27 and 28. The device, numbered 338, comprises a stainless spring steel ring shaped rod 340 having a relaxed condition illustrated in FIG. 28. The rod 340 is severed rather than forming a complete ring, and one end thereof carries a ball 342 while the other end thereof carries a mating socket 344 adapted for receiving the ball when the rod is extended to full ring diameter as illustrated in FIG. 27. A connecting lead 346 is employed for coupling the ring as an external connection in place of the hereinbefore mentioned electrode means 5.

The ring device 338 is normally carried in the distended condition illustrated in FIG. 27 and may be slipped onto the patient's finger after which the ball 342 is sprung out of the socket 344 causing the ring device to grasp tightly the finger of the patient and provide a desired external electrical connection.

Another device for making external connection to a patient's extremity is illustrated in FIGS. 29 and 30. This device, numbered 348, comprises a malleable metal ring or bracelet band 350 internally carrying a metal socket 352 to which there is secured sponge material 354 or other absorbent means adapted to be moistened with a penetrant and/or electrolyte such as silver chloride, DMSO, a saline solution or the like. The wire lead 356 is utilized for connecting the device to the hereinbefore described circuitry in place of electrode means 5. The penetrant contacts the patient.

FIG. 31 illustrates another "external" electrode means and comprises a needle 358 such as an "IV" needle, hypodermic needle or the like which the patient's condition may necessitate. Such needle, connected to the hereinbefore described circuitry by lead 360, may be utilized as the second apparatus connection in place of the electrode means 5 in FIG. 1.

Other types of external terminals or electrodes are possible such as well known adhesive materials and terminals which are electrically conducting.

The external electrode means of the type illustrated for example in FIGS. 25–31 are advantageously employed for relatively rapid and certain connection of the patient to the system according to the present invention, in combination with the airway 10 as illustrated in FIG. 1. Thus, in the case of an unconscious patient suffering from a possible heart attack, the airway 10 is very readily and rapidly inserted in the person's throat in the same manner as an airway is frequently inserted in a patient's throat by a physician for the purpose of delivering mouth-to-mouth resuscitation. The external electrode, for example the clamping devices of FIGS. 25 or 26, are also rapidly connected to an extremity, flap of skin or the like for certainly connecting the patient to the system in the shortest possible period of time. If, as a matter of fact, the patient is not unconscious, he will eject the airway, but a device of the FIG. 24 or FIG. 25 type may be attached to the patient's mouth whereby continual monitoring of the patient's condition is possible.

In the following claims, the term "non-cardiac", when applied to measurement, refers to measurement of other than the heart beat itself.

While we have shown and described several embodiments of our invention, it will be apparent to those skilled in the art that many changes and modifications may be made without departing from our invention in its broader aspects. We, therefore, intend the appended claims to cover all such changes and modifications as fall within the true spirit and scope of our invention.

We claim:

1. A cardiac resuscitator apparatus comprising:

an oro-pharyngeal airway for insertion into the pharynx of a patient, said airway having contact means mounted thereon for making electrical contact with tissue within the patient, second electrode means for external placement on the patient in the chest-abdominal region for making electrical contact with the patient in said region, circuit means for generating an electrical defibrillating pulse, said circuit means having first and second terminals between which said defibrillating pulse is supplied, and conductor means respectively coupling said first and second terminals to said contact means and said second electrode means for delivering said defibrillating pulse to the patient through a current pathway in the trunk of the patient between said contact means mounted on said airway and said second electrode means for defibrillating the patient's heart.

2. A cardiac resuscitator apparatus comprising:

an oro-pharyngeal airway for insertion into the pharynx of a patient, said airway having contact means mounted thereon for making electrical contact with tissue within the patient, second electrode means for external placement on the patient in the chest-abdominal region for making electrical contact with the patient in said region, first circuit means connected to said contact means on said airway for deriving an electrical input from the patient's heart for detecting an abnormal heart condition, second circuit means for generating a defibrillating pulse, said second circuit means having first and second terminals between which said defibrillation pulse is supplied, said second circuit means being responsive in its operation to detection of an abnormal heart condition by said first circuit means, and conductor means for respectively connecting said first and second terminals to said contact means and said second electrode means for delivering said defibrillating pulse to the patient through a current pathway in the trunk of the patient between said contact means mounted on said airway and said second electrode means for defibrillating the patient's heart.

3. A cardiac resuscitator apparatus comprising:

an oro-pharyngeal airway for insertion into the pharynx of a patient, said airway having contact means mounted thereon for making electrical contact with tissue within the patient, second electrode means for electrically contacting the patient at another location remote from said contact means, electrical detecting means mounted on said airway and responsive to the patient's respiration by the detection of the flow of air past said detecting means on said airway, first circuit means connected at least to contact means on said airway and to said electrical detecting means for ascertaining the presence of heart associated electrical activity above a predetermined level together with the absence of respiration above a predetermined level for thereupon making a logical determination of a fibrillation condition, second circuit means for generating an electrical defibrillating pulse, said second circuit means being coupled to said first circuit means and responsive to said first circuit means for generating said defibrillating pulse in response to said logical determination of a fibrillation condition, and conductor means for coupling said second circuit means to contact means on said airway and to said second electrode means for delivering said defibrillating pulse to the patient through a current pathway in the trunk of the patient between said contact means and said second electrode means for defibrillating the patient's heart.

4. The resuscitator apparatus according to claim 3 wherein said electrical detecting means for detecting respiration comprises a microphone mounted on said airway responsive to the sound caused by said flow of air.

5. The resuscitator apparatus according to claim 4 wherein said microphone is mounted proximate the forward end of said airway in non-obstructive relation to the passage of air along said airway.

6. The resuscitator apparatus according to claim 4 further including amplifier means coupled to the said microphone and responsive to respiration of the patient due to the flow of air past said microphone, and means for coupling the output of said amplifier means in driving relation to said first circuit means.

7. The resuscitator apparatus according to claim 4 wherein said second electrode means comprises an abdominal electrode for placement on the patient in the chest-abdominal region for making electrical contact with the patient in said region.

8. The resuscitator apparatus according to claim 4 further including pacing means for supplying a regular pacing pulse to the patient via contact means on said airway and said second electrode means in the substantial absence of electrical activity and respiration as detected by said first circuit means.

9. The resuscitator apparatus according to claim 4 further including means for checking the electrical continuity between said contact means mounted on said airway and said second electrode means and the patient.

10. The resuscitator apparatus according to claim 4 wherein said second circuit means for generating said defibrillating pulse includes timing means, and means for ascertaining the output of said first circuit means a predetermined time after the generation of a defibrillating pulse for initiating a second defibrillating pulse.

11. The cardiac resuscitator apparatus according to claim 10 wherein said means for generating an electrical defibrillating pulse further includes timing means for disabling the generation of a defibrillating pulse after the generation of a predetermined number of defibrillating pulses.

12. A cardiac resuscitator apparatus comprising:

an oro-pharyngeal airway for insertion into the pharynx of a patient, said airway having contact means mounted thereon for making electrical contact with tissue within the patient, second electrode means for external placement on the patient in the chest-abdominal region for making electrical contact with the patient in said region, a microphone mounted on said airway for detecting the respiration of the patient by detecting a patient's breath sounds caused by the flow of air past said microphone on said airway, first circuit means connected to said contact means on said airway and to said second electrode means for ascertaining the presence of heart associated electrical activity above a predetermined level, second circuit means connected to said microphone for detecting a patient's respiration above a predetermined level, logical circuit means coupled to said first circuit means and said second circuit means for making a logical determination of the presence of heart associated electrical activity above a predetermined level together with the absence of respiration above a predetermined level for indicating a fibrillation condition, fourth circuit means for generating an electrical defibrillating pulse, said fourth circuit means being coupled to said logical circuit means and responsive to the logical determination thereof for generating said defibrillating pulse in response to determination of a defibrillation condition, and conductor means for coupling said fourth circuit means to said contact means on said airway and to said second electrode means for delivering said defibrillating pulse to the patient through a current pathway in the trunk of the patient between said contact means and said second electrode means for defibrillating the patient's heart.

13. The cardiac resuscitator apparatus according to claim 12 further including pacing means for generating a regular pacing pulse, said pacing means being responsive to said logical circuit means for generating said pacing pulse in the absence of heart associated electrical activity of the patient above a predetermined level together with the absence of respiration above a predetermined level, and conductor means for coupling the output of said pacing means to said contact means on said airway and to said second electrode means for delivering said pacing pulse to the patient through a current pathway in the trunk of the patient between said contact means and said second electrode means for pacing the patient's heart.

14. A cardiac resuscitator apparatus comprising:

first means for insertion into the region of a patient's mouth, said insertion means comprising electrical contact means for contacting the patient's tongue, external electrode means for placement on the patient in the chest-abdominal region for making electrical contact with the patient in said region, circuit means for generating an electrical defibrillating pulse, said circuit means having first and second terminals between which said defibrillation pulse is supplied, and connection means respectively coupling said first and second terminals to said contact means and said external electrode means for delivering said defibrillating pulse to the patient through a current pathway in the trunk of the patient between said contact means and said external electrode means for defibrillating the patient's heart.

15. The resuscitator according to claim 14 further including detection means connected to said contact means and electrode means for detecting the level of electrical heart activity of the patient, said circuit means being responsive in its pulse generating operation to said detection.

16. The resuscitator according to claim 15 further including means mounted on said first means for detecting respiration of the patient, said circuit means for generating an electrical defibrillating pulse being responsive thereto for inhibiting the application of a defibrillating pulse to the patient in the presence of respiration detection.

17. The resuscitator according to claim 16 further including means for generating a pacing pulse, and means for supplying said pacing pulse between said contact means and said electrode means.

18. A life sign monitoring system comprising:

a device for at least partial insertion into or onto a body cavity or passageway of a patient, said device having contact means mounted thereon for contacting tissue on the interior of said cavity or passageway, second electrode means for contacting the patient, said second electrode means comprising means for securely fastening to the patient at a substantially external location remote from said contact means, said second electrode means comprising a ring adapted to grasp an extremity of the patient and provided with ball and socket means for holding the ring in an extended no-grasping condition for initial placement upon an extremity of a patient, and output means coupled to said contact means and said second electrode means for providing cardiac information in response to electrical signals coupled from said contact means and said second electrode means.

19. A life sign monitoring system comprising:

an airway adapted to be passed into the pharynx of a patient, contact means mounted on said airway, first means connected to said contact means for responding to electrical activity associated with the patient's heart, second means for sensing bodily movement of said patient, said second means comprising a sensor applied elsewhere to the body of the patient and responsive to chest expansion of the patient with respiration, said sensor comprising a strain gauge mounted upon means extending at least part way around the patient's chest comprising hinged tongs adapted to carry said strain gauge wherein said strain gauge is pressure-responsive and is disposed between said tongs and the patient's body, and logical means responsive to said first and said second means for indicating the presence of substantial electrical activity and whether bodily movement substantially accompanies said electrical activity.

20. A life sign monitoring system comprising:

an airway adapted to be passed into the pharynx of a patient, contact means mounted on said airway, first means connected to said contact means for responding to electrical activity associated with the patient's heart, second means for sensing bodily movement of said patient, said second means comprising means for detecting the flow of blood in the patient, the last mentioned means including sound-sensing means, amplifier means, and filtering means responsive to blood flow sounds indicative of a sign of life, and multivibrator means responsive to blood flow indicating input from said amplifier means for standardizing the input therefrom, and integrating means for receiving the output of said multivibrator means, and logical means responsive to said first and second means for indicating the presence of substantial electrical activity and whether bodily movement substantially accompanies said electrical activity.

*21. The resuscitator apparatus according to claim 14 wherein said first means for insertion further comprises an intratracheal tube, said electrical contact means being mounted on said intratracheal tube.*

*22. A cardiac resuscitator apparatus comprising:*

*(a) an oro-pharyngeal airway for insertion into the pharynx of a patient, said airway having contact means mounted thereon for making electrical contact with tissue within the patient;*

*(b) second electrode means for external placement on the patient in the chest-abdominal region for making electrical contact with the patient in said region;*

*(c) circuit means for generating an electrical pacing pulse, said circuit means having first and second terminals between which said pacing pulse is supplied; and*

*(d) conductor means respectively coupling said first and second terminals to said contact means and said second electrode means for delivering said pacing pulse to the patient through a current pathway in the trunk of the patient between said contact means mounted on said airway and said second electrode means for pacing the patient's heart.*

*23. The resuscitator apparatus according to claim 22 wherein said circuit means further includes means for repetitively generating said pacing pulse at a predetermined rate.*

*24. A cardiac resuscitator apparatus comprising:*

*(a) an oro-pharyngeal airway for insertion into the pharynx of a patient, said airway having contact means mounted thereon for making electrical contact with tissue within the patient;*

*(b) second electrode means for external placement on the patient in the chest-abdominal region for making electrical contact with the patient in said region;*

*(c) first circuit means connected to said contact means on said airway for deriving an electrical input from the patient's heart for detecting an abnormal heart condition;*

*(d) second circuit means for generating a pacing pulse, said second circuit means having first and second terminals between which said pacing pulse is supplied, said second circuit means being responsive in its operation to detection of an abnormal heart condition by said first circuit means; and*

*(e) conductor means for respectively connecting said first and second terminals to said contact means and said second electrode means for delivering said pacing pulse to the patient through a current pathway in the trunk of the patient between said contact means mounted on said airway and said second electrode means for pacing the patient's heart.*

*25. A cardiac resuscitator apparatus comprising:*

*(a) an oro-pharyngeal airway for insertion into the pharynx of a patient, said airway having contact means mounted thereon for making electrical contact with tissue within the patient;*

*(b) second electrode means for electrically contacting the patient at another location remote from said contact means;*

*(c) electrical detecting means mounted on said airway and responsive to the patient's respiration by the detection of the flow of air past said detecting means on said airway;*

*(d) first circuit means connected at least to contact means on said airway and to said electrical detecting means for ascertaining the substantial absence of heart associated electrical activity together with the absence of respiration above a predetermined level for thereupon making a logical determination of a cardiac arrest condition;*

*(e) second circuit means for generating an electrical pacing pulse, said second circuit means being coupled to said first circuit means and responsive to said first circuit means for generating said pacing pulse in response to said logical determination of a cardiac arrest condition; and*

*(f) conductor means for coupling said second circuit means to contact means on said airway and to said second electrode means for delivering said pacing pulse to the patient through a current pathway in the trunk of the patient between said contact means and said second electrode means for pacing the patient's heart.*

*26. The resuscitator apparatus according to claim 25 wherein said electrical detecting means for detecting respiration comprises a microphone mounted on said airway responsive to the sound caused by said flow of air.*

*27. The resuscitator apparatus according to claim 26 wherein said microphone is mounted proximate the forward end of said airway in non-obstructive relation to the passage of air along said airway. g*

*28. The resuscitator apparatus according to claim 26 further including amplifier means coupled to said microphone and responsive to respiration of the patient due to the flow of air past said microphone, and means for coupling the output of said amplifier means in driving relation to said first circuit means.*

*29. The resuscitator apparatus according to claim 25 wherein said second electrode means comprises an abdominal electrode for placement on the patient in the chest-abdominal region for making electrical contact with the patient in said region.*

*30. The resuscitator apparatus according to claim 25 further including means for checking the electrical continuity between said contact means mounted on said airway and said second electrode means and the patient.*

*31. The resuscitator apparatus according to claim 25 wherein said second circuit means includes means for*

*repetitively generating said pacing pulse at a predetermined rate.*

*32. A cardiac resuscitator apparatus comprising:*

*(a) an oro-pharyngeal airway for insertion into the pharynx of a patient, said airway having contact means mounted thereon for making electrical contact with tissue within the patient;*

*(b) second electrode means for external placement on the patient in the chest-abdominal region for making electrical contact with the patient in said region;*

*(c) a microphone mounted on said airway for detecting the respiration of the patient by detecting a patient's breath sounds caused by the flow of air past said microphone on said airway;*

*(d) first circuit means connected to said contact means on said airway and to said second electrode means for ascertaining the absence of heart associated electrical activity of the patient above a predetermined level;*

*(e) second circuit means connected to said microphone for detecting a patient's respiration above a predetermined level;*

*(f) logical circuit means coupled to said first circuit means and said second circuit means for making a logical determination of the absence of heart associated electrical activity above a predetermined level together with the absence of respiration above a predetermined level for indicating a cardiac arrest condition;*

*(g) fourth circuit means for generating an electrical pacing pulse, said fourth circuit means being coupled to said logical circuit means and responsive to the logical determination thereof for generating said pacing pulse in response to determination of a cardiac arrest condition; and*

*(h) conductor means for coupling said fourth circuit means to said contact means on said airway and to said second electrode means for delivering said pacing pulse to the patient through a current pathway in the trunk of the patient between said contact means and said second electrode means for pacing the patient's heart.*

*33. A cardiac resuscitator apparatus comprising:*

*(a) first means for insertion into the region of a patient's mouth, said first means comprising electrical contact means for contacting the patient's tongue;*

*(b) external electrode means for placement on the patient in the chest-abdominal region for making electrical contact with the patient in said region;*

*(c) circuit means for generating an electrical pacing pulse, said circuit means having first and second terminals between which said pacing pulse is supplied; and*

*(d) connection means respectively coupling said first and second terminals to said contact means and said external electrode means for delivering said pacing pulse to the patient through a current pathway in the trunk of the patient between said contact means and said external electrode means for pacing the patient's heart.*

*34. The resuscitator according to claim 33 further including detection means connected to said contact means and electrode means for detecting the level of electrical heart activity of the patient, said circuit means being responsive in its pulse generating operation to said detection.*

*35. The resuscitator apparatus according to claim 33 wherein said circuit means includes means for repetitively generating said pacing pulse at a predetermined rate.*

*36. The resuscitator apparatus according to claim 33 further including means for detecting a heart beat, said circuit means for generating a pacing pulse being responsive thereto for inhibiting the generation of said pacing pulse in the presence of a patient heart beat of acceptable rate.*

*37. The resuscitator apparatus according to claim 33 wherein said first means for insertion further comprises an intratracheal tube, said electrical contact means being mounted on said intratracheal tube.*

*38. A life sign monitoring system comprising:*

*(a) a tube adapted to be passed at least into the pharynx of a patient;*

*(b) contact means mounted on said tube;*

*(c) first means connected to said contact means for responding to electrical activity associated with the patient's heart;*

*(d) second means for sensing bodily movement of said patient, said second means comprising a sensor applied elsewhere to the body of the patient and responsive to chest expansion of the patient with respiration, said sensor comprising a strain gauge mounted upon means extending at least part way around the patient's chest comprising hinged tongs adapted to carry said strain gauge wherein said strain gauge is pressure-responsive and is disposed between said tongs and the patient's body; and*

*(e) logical means responsive to said first and said second means for indicating the presence of substantial electrical activity and whether bodily movement substantially accompanies said electrical activity.*

*39. The life sign monitoring system according to claim 38, wherein said tube is adapted to be passed into the trachea of a patient.*

*40. A life sign monitoring system comprising:*

*(a) a tube adapted to be passed at least into the pharynx of a patient;*

*(b) contact means mounted on said tube;*

*(c) first means connected to said contact means for responding to electrical activity associated with the patient's heart;*

*(d) second means for sensing bodily movement of said patient, said second means comprising means for detecting the flow of blood in the patient, the last mentioned means including sound-sensing means, amplifier means, and filtering means responsive to blood flow sounds indicative of a sign of life, and multivibrator means responsive to blood flow indicating input from said amplifier means for standardizing the input therefrom, and integrating means for receiving the output of said multivibrator means; and*

*(e) logical means responsive to said first and second means for indicating the presence of substantial electrical activity and whether bodily movement substantially accompanies said electrical activity.*

*41. The life sign monitoring system according to claim 40, wherein said tube is adapted to be passed into the trachea of a patient.*

* * * * *